United States Patent [19]

Deninno et al.

[11] Patent Number: 5,629,295
[45] Date of Patent: May 13, 1997

[54] STEROIDAL GLYCOSIDES FOR TREATING HYPERCHOLESTEROLEMIA

[75] Inventors: Michael P. Deninno, Gales Ferry; Peter A. McCarthy, Pawcatuck, both of Conn.

[73] Assignee: Pfizer Inc., New York, N.Y.

[21] Appl. No.: 351,470

[22] PCT Filed: May 6, 1993

[86] PCT No.: PCT/US93/04092

§ 371 Date: Dec. 20, 1994

§ 102(e) Date: Dec. 20, 1994

[87] PCT Pub. No.: WO94/00480

PCT Pub. Date: Jan. 6, 1994

Related U.S. Application Data

[63] Continuation-in-part of Ser. No. 904,914, Jun. 26, 1992, abandoned.

[51] Int. Cl.$^6$ .......................... A61K 31/705; A61K 31/56
[52] U.S. Cl. .......................... 514/26; 514/177; 514/178; 514/182; 514/824; 536/5
[58] Field of Search ..................... 514/26, 824, 177, 514/178, 182; 536/5

[56] References Cited

U.S. PATENT DOCUMENTS

| | | | |
|---|---|---|---|
| 4,260,603 | 4/1981 | Pegel et al. | 536/5 |
| 4,265,886 | 5/1981 | Pegel et al. | 536/5 |
| 4,461,762 | 7/1984 | Malinow | 536/5 |
| 4,552,868 | 11/1985 | Jarreau et al. | 514/26 |
| 4,584,289 | 4/1986 | Jarreau et al. | 514/182 |
| 4,602,003 | 7/1986 | Malinow | 514/26 |
| 4,602,005 | 7/1986 | Malinow | 514/26 |
| 4,885,280 | 12/1989 | Jarreau et al. | 514/26 |
| 5,010,185 | 4/1991 | Urban | 536/6.1 |
| 5,017,562 | 5/1991 | Holmes et al. | 536/6 |
| 5,530,107 | 6/1996 | Douglas et al. | 536/6.1 |

FOREIGN PATENT DOCUMENTS

| | | |
|---|---|---|
| 0020029 | 12/1980 | European Pat. Off. |
| 0159431 | 10/1985 | European Pat. Off. |
| 0403150 | 12/1990 | European Pat. Off. |
| 9302048 | 7/1992 | WIPO |
| 9305790 | 9/1992 | WIPO |
| 9307167 | 9/1992 | WIPO |
| 9311150 | 10/1992 | WIPO |
| 9417038 | 1/1994 | WIPO |

OTHER PUBLICATIONS

Freire et al. *Chromatography in Biochemistry, Medicine and Environmental Research* vol. 1 pp. 249–259, (1983).
Woo et al. *J. Natl. Products*, vol. 55(8), pp. 1129–1135, (1992). Abstract only.
Tsung et al. *Hua Hsueh Hsueh Pao*, vol. 34(3), pp. 179–196, (1976) Abstract Only.
Malinow, M. R. et al., Annals of the N.Y. Academy of Sciences, 454 (Atherosclerosis); 23–27, 1985.
Dimoglo et al., Chemical Abstracts, 103:66658x, 1985.
Sidhu et al., Chemical Abstracts, 107:22075h, 1987.
Nakano et al., Phytochemistry 30 (6), 1993–1995, 1991.
"Effects of Alpha–and Beta–Tigogenin Cellobiosides on Cholesterol Absorption" Malinow, M.R. et al.; Steroids Structure, Function, and Regulation; 48(3–4), 197–211; 1986.
"Determination of the Absolute Configuration of a Secondary Hydroxy Group in a Chiral Secondary Alcohol Using Glycosidation Shifts in Carbon–13 NMR Spectroscopy" Seo, S.; Tomita, Y.; Tori, K.; Yoshimura, Y.; J. Am. Chem. Soc. 100(11), 3331–3339, 1978.
"Glycosidation Shifts in Carbon–13 NMR Spectroscopy: Carbon–13 Signal Shifts from Aglycone and Glucose to Glucoside" Tori, K.; Yoshimura, Y.; Arita, H.; Tomita, Y.; Tetrahed. Lett. (2), 179–182, 1977.
"Chemistry of Ayurvedic Crude Drugs: Part VIII–Shatavari–2: Structure Elucidation of Bioactive Shatavarin–I and Other Glycosides" Joshi, J.; Dev, S.; Ind. J. Chem 27B, 12–16, 1988.
"Molluscicidal Saponins from Cornus Florida L." Hostettmann, K.; Hostettmann–Kaldas, M.; Nakanishi, K.; Helv. Chim. Acta 61, 1990–1995, 1978.
"Carbon–13 NMR Spectroscopy of Steroidal Sapogenins and Steroidal Saponins" Agrawal, P.K.; Jain, D.C.; Gupta, R.K. Thakur, R.S.; Phytochemistry 24 (11), 2479–2496, 1985.
"Studies on the Constituents of Asparagi Radix. I. On the Structures of Furostanol Oligosides of Asparagus Cochinchinensis Merrill" Konishi, T.; Shoji, J.; Chem. Pharm. Bull. 27 (12), 3086–3094, 1979.
"Saponins of the Spirostanol Series. XII. Parillin, A Saponin with a Highly Branched Sugar Chain" Tschesche, R.; Kottler, R.; Wulff, G.; Just. Liebigs Ann. Chem. 699, 212–222, 1966.
"Damaging Effects of Saponins on Termites" Tschesche, R.; Wulff, G.; Weber, A.; Schmidt, H.Z.; Naturforsch. B 25 (9) 999–1001, 1970.
"Medicinal Asparagus (Asparagus Officinalis L.) as a Source of Steroidal Glycosides" Goryanu, G.M.; Krokhmalyuk, V.V.; Kintya, P.K.; Glyzin, V.I.; Farmatsiya (Moscow) 25 (4), 66–7, 1976.
"Two New Steroidal Glucuronides From Solanum Lyratum, II" Yahara, S.; Morooka, M.; Ikeda, M.; Yamasaki, M.; Nohara, T.; Planta Med. (6) 496–8, 1986.

(List continued on next page.)

*Primary Examiner*—John Kight
*Assistant Examiner*—Howard C. Lee
*Attorney, Agent, or Firm*—Peter C. Richardson; Gregg C. Benson; A. Dean Olson

[57] ABSTRACT

The application discloses steroidal glycoside compounds, especially spirostanyl glycosides, which have a glycosyl group O-linked to the C-3 hydroxy radical of the steroid and where the moieties at the C-10 and C-11 positions of the steroid are the same or different and are selected from the group consisiting of methylene, hydroxy and carbonyl. These steroid glycosides are useful as hypocholesterolemic agents and anti-atherosclerosis agents.

36 Claims, No Drawings

OTHER PUBLICATIONS

"Preparation and properties of Some New Steroid Beta-D-Glucopyranosides, Beta-D-Glucopyranosiduronic Acids, and Derivatives" Schneider, J.; J. Carb. Research 17, 199–207, 1971.

"Structure Activity Relationships in Steroid Glycosides" Dimolgo, A.S.; Choban, I.N.; Bersuker, I.B.; Kintya, P.K.; Khim. Far., Zh. 19 (2), 185–9, 1985.

"Modifiers of Bilayer Lipid Membranes Among Steroid Glycosides" Bogatskii, A.V.; Nazarova, N. Yu.; Kintya, P.K.; Bobeiko, V.A.; Dokl. Akad. Nauk, SSSR (Biophys) 252 235–7, 1980.

"Steroidal Saponins from Several Species of Lilliflorae Plants" Yang, C.; Li, K.; Ding, Y.; Yunnan Zhiwu Yanjiu Zengkan, Suppl. 3, 13–23, 1990.

"Search for Hypocholesterolemic Agents Steroid Glycosides" Kintya, P.K.; Vasilenko, I.K.; Gorianu, G.M.; Bobeiko, V.A.; Suetina, I.V.; Mashchenko, N.E. Khim. Farm. Zh. 15 (9), 55–60, 1981. (Translation provided).

"Steroid Glycosides from the Leaves of Agave Americana" Lazurevskii, G.V.; Bobeiko, V.A.; Kintya, P.K.; Dokl. Akad. Nauk. SSSR 224 (6), 1442–1444, 1975. (Translation provided).

"Steroid Glycosides from Asparagus Officinalis" Lazurevskii, G.V.; Goryanu, G.M.; Kintya, P.K.; Dokl. Akad. Nauk. SSSR 231 (6), 1479–1481, 1976. (Translation provided).

"Steroid Saponins XVII: The Structure of Asparagosides D and G." Goryanu, G.M., Kintya, P.K.; Khim. Prir. Soedin. (6) 762–765, 1976. (Translation provided).

"The Structure of the Glycosides of Asparagus Officinalis. The Structure of Asparagosides A and B." Goryanu, G.M.; Krokhmalyuk, V.V.; Kintya, P.K.; Khi, Prir. Soedin. (3), 400–401, 1976. (Translation provided).

"Steroidal Glycosides XXII; Rockogenin glycosides." Kintya, P.K.; Bobeiko, V.A.; Khim. Prir. Soedin. (1) 102–103, 1979. (Translation provided).

"Hemolytic Properties of Synthetic Glycosides." Segal, R.; Shud, F.; Milo–Goldzweig, I.; J. Pharm. Sci. 67 (11) 1589–1592, 1978.

"Saponins in the Leaves of Agave Americana." Kintya, P.K.; Bobeiko, V.A.; Krokhmalyuk, V.V.; Chivra, V. Ya. Pharmazie 30 (6), 396–7, 1975.

"Steroid Glycosides from the Roots of Capsicum Annum II: The Structure of the Capsicosides" Gutsu, E.V.,; Kintya, P.K.; Lazurevskii, G.V.; Khim Prir. Soedin. (2), 242–246, 1987. (Translation provided).

"Steroidal Saponins from a Cultivated form of Agave Sisalana" Ding, Y.; Chen, Y.Y.; Wang, D.Z.; Yang, C.R. Phytochemistry 28(10), 2787–91, 1989.

"Novel Silver Salts in Glycoside Synthesis" Wulff, G.; Rohle, G.; Kruger, W., Chem. Ber. 105, 1097–1110, 1972.

"The Susceptibility of Cholesterol–Depleted Erythrocytes to Saponin and Sapogenin Hemolysis" Segal R., Milo–Goldzweig, I. Biochem. Biophys. Acta 512, 223–226, 1978.

"Steroid Saponins III: Glycosides A and B from Yucca Filamentosa" Kintya, P.K.; Dragalin, I.P.; Chirva, V. Ya. Khim Prir. Soedin (5), 615–616, 1972. (Translation provided).

"Steroidal Glycosides of Tribulus Terrestirs Linn." Mahato, S.B.; Sahu, N.P.; Ganguly, A.N.; Miyahara, K.; Kawasaki, T.J. Chem. Soc. Perkin Trans. I 2405–2410, 1981.

"Structural Freatures of the Antioxidant and Fungicidal Activity of Steroid Glycosides" Dimoglo, A.S.; Choban I.N.; Bersuker, I.B.; Kintya, P.K.; Balashova, N.N. Bioorg. Khim. 11(3), 408–413, 1985. (Translation provided).

STEROIDAL GLYCOSIDES FOR TREATING HYPERCHOLESTEROLEMIA

This application was filed under 35 U.S.C. § 371 based on PCT/US93/04092 application, which was filed on May 6, 1993 and which is a continuation-in-part of U.S. application Ser. No. 07/904,914 which was filed on Jun. 26, 1992 and is now abandoned. Applicants hereby claim priority from all such applications.

BACKGROUND OF THE INVENTION

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives, for example of polystyrene. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficiency. Thus, the effective hypocholesterolemic dose of these materials is excessive, typically 18–24 grams of formulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of nonuseful chemical substances. Due to the variations in composition, it is difficult to set a standard dosage or predict the impurities present. Thus, such extracts are not well suited for use by humans. Furthermore purification of these extracts would be expensive. As an alternative certain synthetically produced, pure "sapogenin-derived" compounds e.g., substances compounded from spirostane, spirostene or sterol-derived compounds depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive mounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, Iu. K. Vasilenko, G. M. Godanu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyramine.

In addition, certain other steroidal glycosides described below have been published, however these publications do not address hypocholesterolemic activity. "Structural Features of the Antioxidant and fungicidal Activity of Steroid Glycosides", Dimoglo, A. S.; Choban I. N.; Bersuker, I. B.; Kintya, P. K.; Balashova, N. N.; Bioorg. Khim, 11 (3), 408–413, 1985 discloses rockogenin β-D-galactopyranoside and tigogenin β-D-lactoside. "Preparation and Properties of Some New Steroid β-D-Glucopyranosides, β-D-Glucopyranosiduronic Acids, and Derivatives", Schneider, J. J.; Carb. Research, 17, 199–207, 1971 discloses tigogenin β-D-glucopyranuronoside. "Sterol Glycoside with Activity as Prostaglandin Synthetase Inhibitor", Pegel, K. H. Walker, H.; U.S. Pat. No. 4,260,603, Apr. 7, 1981 discloses hecogenin β-D-glucopyranoside. "Hemolytic Properties of Synthetic Glycosides", Segal, R.; Shud, F.; Milo-Goldzweig, I.; J. Pharm. Sci. , 67 (11) 1589–1592, 1978 discloses tigogenin β-D-maltosside, tigogenin β-L-fucopyranoside smilagenin β-maltoside and tigogenin α-L-rhamnoside. "Steroid Glycosides from the Roots of Capsicum annuum II: The Structure of the Capsicosides", Gutsu, E. V.; Kintya, P. K.; Lazurevskii, G. V.; Khim. Prir. Soedin., (2), 242–246, 1987 discloses tigogenin α-D-arabanopyranoside and tigogenin β-D-galactopyranoside. "Molluscicidal Saponins from Cornus Florida L.", Hostettmann, K.; Hostettmann- Kaldas, M.; Nakanishi, K.; Helv. Chim. Acta, 61, 1990–1995, 1978 discloses smilagenin β-D-galactopyranoside. "Steroidal Saponins from Several Species of Liliifiorae Plants", Yang, C.; Li, K.; Ding, Y.; Yunnan Zhiwu Yanjiu Zengkan, Suppl. 3, 13–23, 1990 discloses (25S)-hecogenin cellobioside. "Determination of the Absolute Configuration of a Secondary Hydroxy Group in a Chiral Secondary Alcohol Using Glycosidation shifts in Carbon-13 NMR Spectroscopy", Seo, S.; Tomita, Y.; Tori, K.; Yoshimura, Y.; J. Am. Chem. Soc. , 100(11), 3331–3339, 1978 discloses smilagenin β-glucoside and smilagenin α-glucoside. "Steroid Glycosides from Asparagus officinalis", Lazurevskii, G. V.; Goryanu, G. M.; Kintya, P. K.; Dokl. Akad. Nauk. SSSR, 231(6), 1479–81, 1976 discloses sarsasapogenin β-glucoside.

Although the hypocholesterolemic compounds described above make a significant contribution to the art there is a continuing search in this field of art for improved hypocholesterolemic pharmaceuticals.

SUMMARY OF THE INVENTION

This invention is directed to steroidal glycosides, particularly spirostanyl glycosides, that are useful as hypocholesterolemic agents and antiatherosclerosis agents. The compounds of this invention have the formula

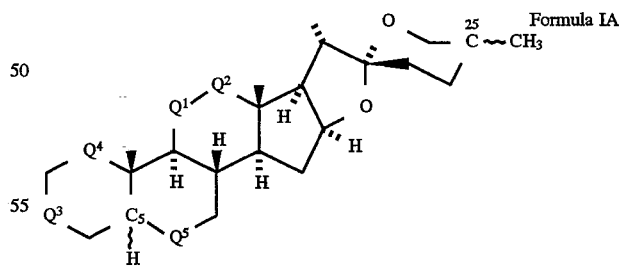

Formula IA wherein either (A):

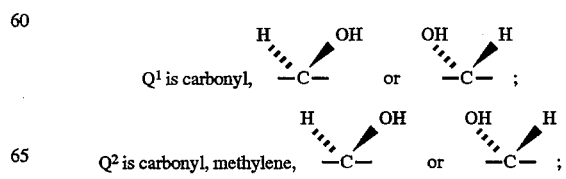

$Q^3$ is 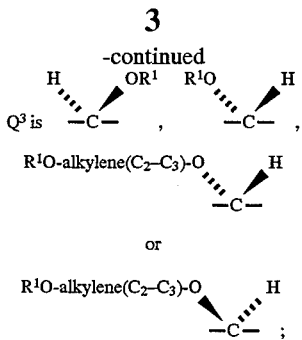

$Q^4$ and $Q^5$ are both methylene;
and wherein
$R^1$ is
β-D-glucopyranosyl,
β-D-glucopyranuronosyl,
β-D-2-acetamido-2-deoxy-glucopyranosyl,
β-D-galactopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
α-D-cellobiosyl,
β-D-cellobiosyl,
β-D-lactosyl,
β-D-maltosyl,
β-D-gentiobiosyl,
3-O-α-D-galactopyranosyl-α-D-arabanopyranosyl or
β-D-maltotriosyl;
or (B):
$Q^1$, $Q^4$ and $Q^5$ are all methylene;

$Q^2$ is 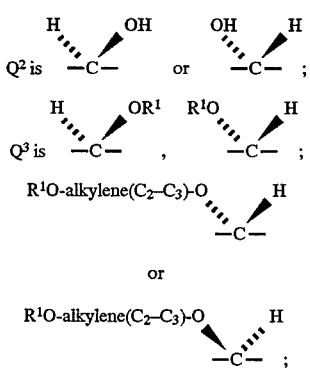

$Q^3$ is and wherein
$R^1$ is
β-D-glucopyranosyl,
β-D-glucopyranuronosyl,
β-D-2-acetamido-2-deoxy-glucopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
β-D-cellobiosyl,
β-D-lactosyl,
β-D-maltosyl,
β-D-gentiobiosyl,
3-O-β-D-galactopyranosyl-α-D-arabanopyranosyl or
β-D-maltotriosyl;
or (C):
$Q^1$, $Q^4$ and $Q^5$ are all methylene;
$Q^2$ is carbonyl;

$Q^3$ is 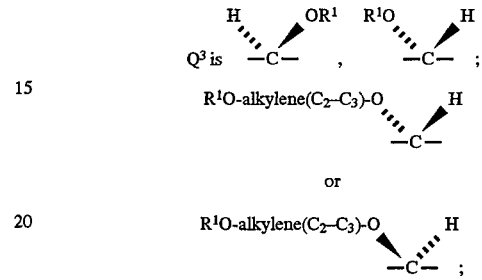

$C_{25}$ is (R);
and wherein
$R^1$ is
β-D-glucopyranuronosyl,
β-D-2-acetarnido-2-deoxy-glucopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
β-D-cellobiosyl,
β-D-lactosyl,
β-D-maltosyl,
β-D-gentiobiosyl,
3-O-β-D-galactopyranosyl-α-D-arabanopyranosyl or
β-D-maltotriosyl;
or (D):
$Q^1$, $Q^2$, $Q^4$ and $Q^5$ are each methylene;
and $Q^3$ is 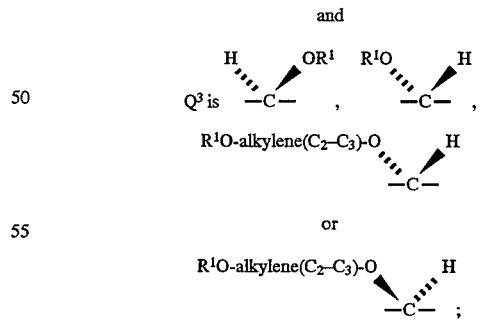

and wherein
$R^1$ is
β-D-2-acetamido-2-deoxy-glucopyranosyl,
β-D-fucopyranosyl,
β-D-xylopyranosyl,
β-L-xylopyranosyl,
α-L-arabanopyranosyl, β-D-cellobiosyl,
β-D-gentiobiosyl,
3-O-β-D-galactopyranosyl-α-D-arabanopyranosyl, or
β-maltotriosyl;
or (E):

$Q^1$, $Q^2$, and $Q^5$ are each methylene;

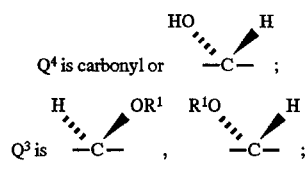

$Q^4$ is carbonyl or ;

$Q^3$ is , ;

$C_5$ is alpha;
$C_{25}$ is (R); and wherein
$R^1$ is
β-D-galactopyranosyl,
β-D-cellobiosyl,
β-D-lactosyl,
β-D-maltosyl or
β-D-maltotriosyl;
or (F):

$Q^1$, $Q^2$, and $Q^4$ are each methylene;

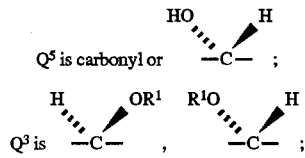

$Q^5$ is carbonyl or ;

$Q^3$ is , ;

$C_5$ is alpha;
$C_{25}$ is (R); and wherein
$R^1$ is
β-D-galactopyranosyl,
β-D-cellobiosyl,
β-D-lactosyl,
β-D-maltosyl or
β-D-maltotriosyl;
with the proviso that (3β,5α,25R)-3-[(β-D-cellobiosyl) oxy]spirostane is not included.

A first group of preferred compounds of Formula IA consists of these compounds wherein $Q^1$ is carbonyl,

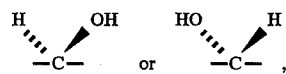

$Q^2$ is methylene, $Q^3$ is

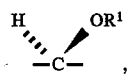

$Q^4$ is methylene, $Q^5$ is methylene, the $C_5$ hydrogen is alpha and $C_{25}$ has the R configuration. Especially preferred within this group are compounds wherein $Q^1$ is carbonyl and $R^1$ is β-D-cellobiosyl, α-D-cellobiosyl, β-D-glucopyranosyl, β-D-galactopyranosyl, β-D-lactosyl, β-D-maltosyl or β-D-maltotriosyl. Also, especially preferred within this group is a compound wherein $Q^1$ is

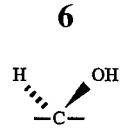

and $R^1$ is β-D-cellobiosyl. Another especially preferred compound within this group is a compound wherein $Q^1$ is

and $R^1$ is β-D-cellobiosyl.

A second group of preferred compounds of Formula IA are compounds wherein $Q^1$ is methylene, $Q^2$ is

$Q^4$ is methylene, $Q^5$ is methylene, the $C_5$ hydrogen is alpha and $C_{25}$ is (R). Especially preferred within this second group is a compound wherein $Q^2$ is

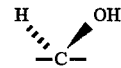

and $R^1$ is β-D-cellobiosyl.

A third group of preferred compounds of Formula IA are compounds wherein $Q^1$ is carbonyl,

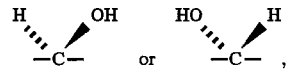

$Q^2$ is carbonyl,

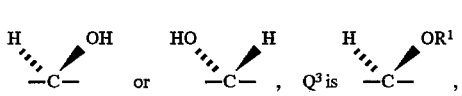

$Q^4$ is methylene, $Q^5$ is methylene, the $C_5$ hydrogen is alpha and $C_{25}$ is (R). Especially preferred within this group is a compound wherein $Q^1$ is carbonyl, $Q^2$ is carbonyl and $R^1$ is β-D-cellobiosyl. Another especially preferred compound within this group is a compound wherein $Q^1$ is carbonyl, $Q^2$ is

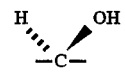

and $R^1$ is β-D-cellobiosyl. Another especially preferred compound within this group is a compound wherein $Q^1$ is carbonyl, $Q^2$ is

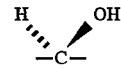

and $R^1$ is β-D-lactosyl. Another especially preferred compound within this group is a compound wherein $Q^1$ is

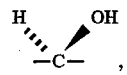

$Q^2$ is carbonyl and $R^1$ is β-D-cellobiosyl. Another especially preferred compound within this group is a compound wherein $Q^1$ is

$Q^2$ is carbonyl and $R^1$ is β-D-cellobiosyl.

A fourth group of preferred compounds of Formula IA are compounds wherein $Q^1$ is methylene, $Q^2$ is carbonyl, $Q^3$ is

$Q^4$ is methylene, $Q^5$ is methylene, the $C_5$ hydrogen is alpha and $C_{25}$ is (R). Especially preferred within this fourth group are compounds wherein $R^1$ is β-D-lactosyl or β-D-cellobiosyl.

A fifth group of preferred compounds of Formula IA are compounds wherein $Q^1$ and $Q^2$ are each methylene, $Q^3$ is

$Q^4$ and $Q^5$ are each methylene and $C_{25}$ is (R). Especially preferred within this fifth group is a compound wherein the $C_5$ hydrogen is alpha and $R^1$ is β-D-gentiobiosyl. Another especially preferred compound within this group is a compound wherein the $C_5$ hydrogen is beta and $R^1$ is β-D-cellobiosyl.

A sixth group of preferred compounds of Formula IA are compounds wherein $Q^1$, $Q^2$ and $Q^5$ are each methylene, $Q^3$ is

$Q^4$ is carbonyl, the $C_5$ hydrogen is alpha and $C_{25}$ is (R). Especially preferred within this group is a compound wherein $R^1$ is β-D-cellobiosyl.

A seventh group of preferred compounds of Formula IA are compounds wherein $Q^1$, $Q^2$ and $Q^4$ are each methylene, $Q^3$ is

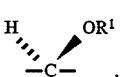

$Q^5$ is carbonyl, the $C_5$ hydrogen is alpha and $C_{25}$ is (R). Especially preferred within this group is a compound wherein $R^1$ is β-D-cellobiosyl.

Yet another aspect of this invention is directed to a method for controlling hypercholesterolemia or atherosclerosis in a mammal by administering to a mammal suffering from hypercholesterolemia or atherosclerosis a hypercholesterolemia or atherosclerosis controlling amount of a Formula I spirostanyl glycoside

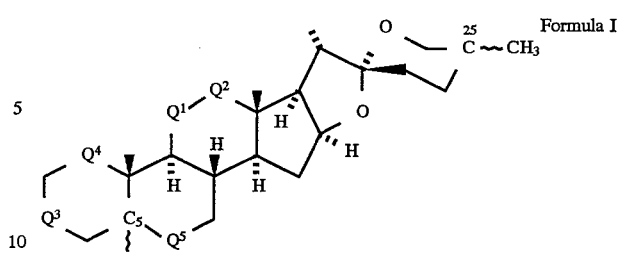

wherein
either (A):

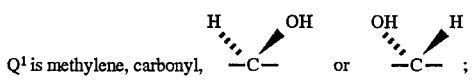

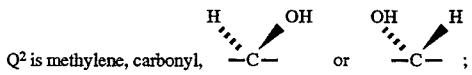

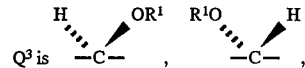

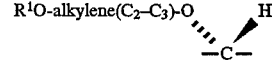

or

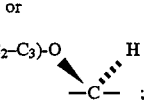

$Q^4$ and $Q^5$ are both methylene;
and wherein
$R^1$ is
  β-D-glucopyranosyl,
  β-D-glucopyranuronosyl,
  β-D-2-acetamido-2-deoxy-glucopyranosyl,
  β-D-galactopyranosyl,
  β-D-fucopyranosyl,
  β-L-fucopyranosyl,
  β-D-xylopyranosyl,
  β-L-xylopyranosyl,
  α-D-arabanopyranosyl,
  α-L-arabanopyranosyl,
  α-D-cellobiosyl,
  β-D-cellobiosyl,
  β-D-lactosyl,
  β-D-maltosyl,
  β-D-gentiobiosyl,
  3-O-β-D-galactopyranosyl-α-D-arabanopyranosyl, or
  β-maltotriosyl;

or (B):

$Q^1$, $Q^2$, and $Q^5$ are each methylene;

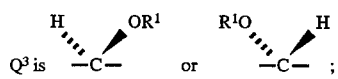

$C_5$ is alpha;
$C_{25}$ is (R);
and wherein
$R^1$ is

β-D-galactopyranosyl,
β-D-cellobiosyl,
β-D-lactosyl,
β-D-maltosyl or
β-D-maltotdosyl;

or (C):

$Q^1$, $Q^2$ and $Q^4$ are each methylene;

$Q^3$ is 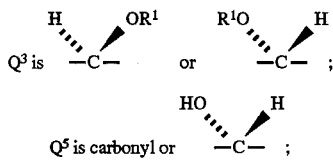

$Q^5$ is carbonyl or 

$C_5$ is alpha;

$C_{25}$ is (R);

and wherein;

$R^1$ is
β-D-galactopyranosyl,
β-D-cellobiosyl,
β-D-lactosyl,
β-D-maltosyl or
β-D-maltotriosyl;

with the proviso that
(3β,5α,25R)-3-[(α-D-cellobiosyl)oxy]spirostane,
(3β,5α,25R)-3-[(β-D-glucopyranosyl)oxy]spirostane,
(3β,5α,25R)-3-[(β-D-cellobiosyl)oxy]spirostane or
(3β,5α,25R)-3-[(β-D-galactopyranosyl)oxy]spirostan-12-one are not included.

A first group of preferred compounds of Formula I are compounds wherein $Q^1$, $Q^2$, $Q^4$ and $Q^5$ are methylene, $C_{25}$ is (R) and $Q^3$ is

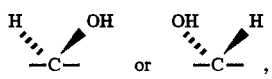

Especially preferred within this group are compounds wherein the $C_5$ hydrogen is alpha and $R^1$ is β-D-glucopyranuronosyl, β-D-maltosyl, β-D-lactosyl, β-D-gentiobiosyl or β-D-galactopyranosyl. Another especially preferred compound within this group is a compound wherein the $C_5$ hydrogen is beta and $R^1$ is β-D-cellobiosyl.

A second group of preferred compounds of Formula I are compounds wherein $Q^1$ is carbonyl,

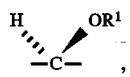

$Q^2$ is methylene, $Q^3$ is

$Q^4$ and $Q^5$ are each methylene, $C_{25}$ is (R) and the $C_5$ hydrogen is alpha. Especially preferred within this second group are compounds wherein $Q^1$ is carbonyl and $R^1$ is β-D-cellobiosyl, α-D-cellobiosyl, β-D-glucopyranosyl, β-D-galactopyranosyl, β-D-lactosyl, β-D-maltosyl or β-D-maltotdosyl. Another especially preferred compound within this second group is a compound wherein $Q^1$ is

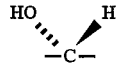

and $R^1$ is β-D-cellobiosyl. Another especially preferred compound within this second group is a compound wherein $Q^1$ is

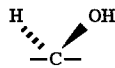

and $R^1$ is β-D-cellobiosyl.

A third group of preferred compounds of Formula I are compounds wherein $Q^1$ is methylene, $Q^2$ is carbonyl,

$Q^4$ and $Q^5$ are each methylene, $C_{25}$ is (R) and the $C_5$ hydrogen is alpha. Especially preferred within this third group are compounds wherein $Q^2$ is carbonyl and $R^1$ is β-D-cellobiosyl or β-D-lactosyl. Other especially preferred compounds within this third group are compounds wherein $Q^2$ is

and $R^1$ is β-D-cellobiosyl or β-D-galactopyranosyl.

A fourth group of preferred compounds of Formula I are compounds wherein $Q^1$ is carbonyl,

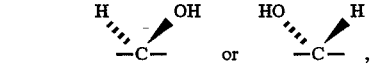

$Q^2$ is carbonyl,

$Q^4$ and $Q^5$ are each methylene, the $C_5$ hydrogen is alpha and $C_{25}$ is (R). Especially preferred within this fourth group is a compound wherein $Q^1$ is carbonyl, $Q^2$ is carbonyl and $R^1$ is β-D-celiobiosyl. Especially preferred within this fourth group are compounds wherein $Q^1$ is carbonyl, $Q^2$ is

and $R^1$ is β-D-cellobiosyl or β-D-lactosyl. Another especially preferred compound within this group is a compound wherein $Q^1$ is

$Q^2$ is carbonyl, and $R^1$ is β-D-cellobiosyl. Another especially preferred compound within this group is a compound wherein $Q^1$ is

$Q^2$ is carbonyl and $R^1$ is β-D-cellobiosyl.

A fifth group of preferred compounds of Formula I are compounds wherein $Q^1$, $Q^2$ and $Q^5$ are each methylene, $Q^3$ is

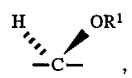

$Q^4$ is carbonyl, the $C_5$ hydrogen is alpha and $C_{25}$ is (R). Especially preferred within this group is a compound wherein $R^1$ is β-D-cellobiosyl.

A sixth group of preferred compounds of Formula I are compounds wherein $Q^1$, $Q^2$ and $Q^4$ are each methylene, $Q^3$ is $Q^5$ is carbonyl, the $C_5$ hydrogen is alpha and $C_{25}$ is (R). Especially preferred within this group is a compound wherein $R^1$ is β-D-cellobiosyl.

This invention is also directed to pharmaceutical compositions for the control of hypercholesterolemia or atherosclerosis in mammals which comprise a compound of the Formula IA and a pharmaceutically acceptable carrier.

Yet another aspect of this invention is directed to a composition comprising a hydrate of a compound of the Formula 1A.

The compounds of Formulas IA and I are herein defined as the single enantiomer having the absolute stereochemistry depicted in Formulas IA and I respectively.

Other features and advantages will be apparent from the specification and claims which describe the invention.

DETAILED DESCRIPTION OF THE INVENTION

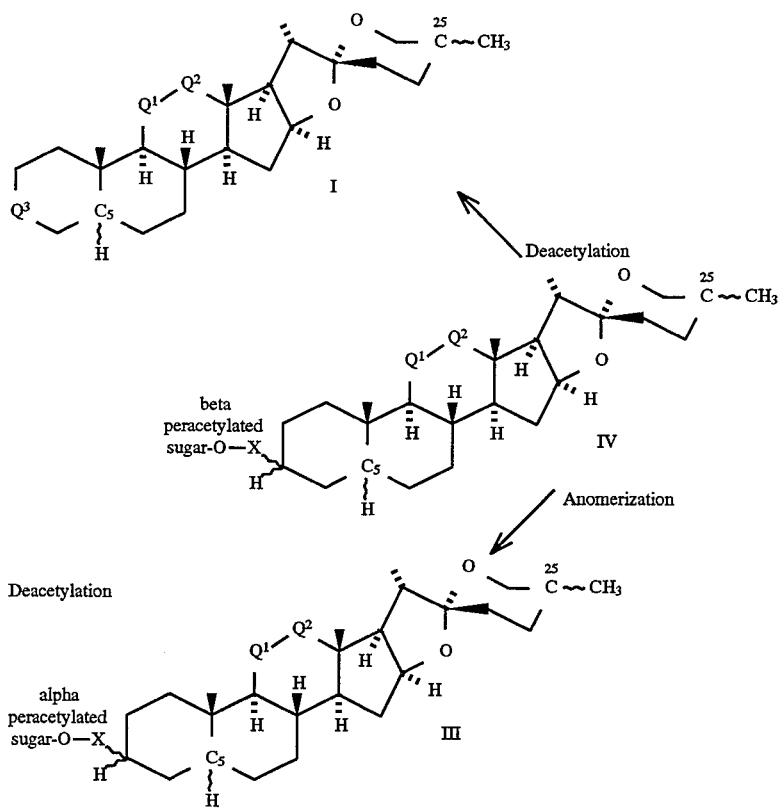

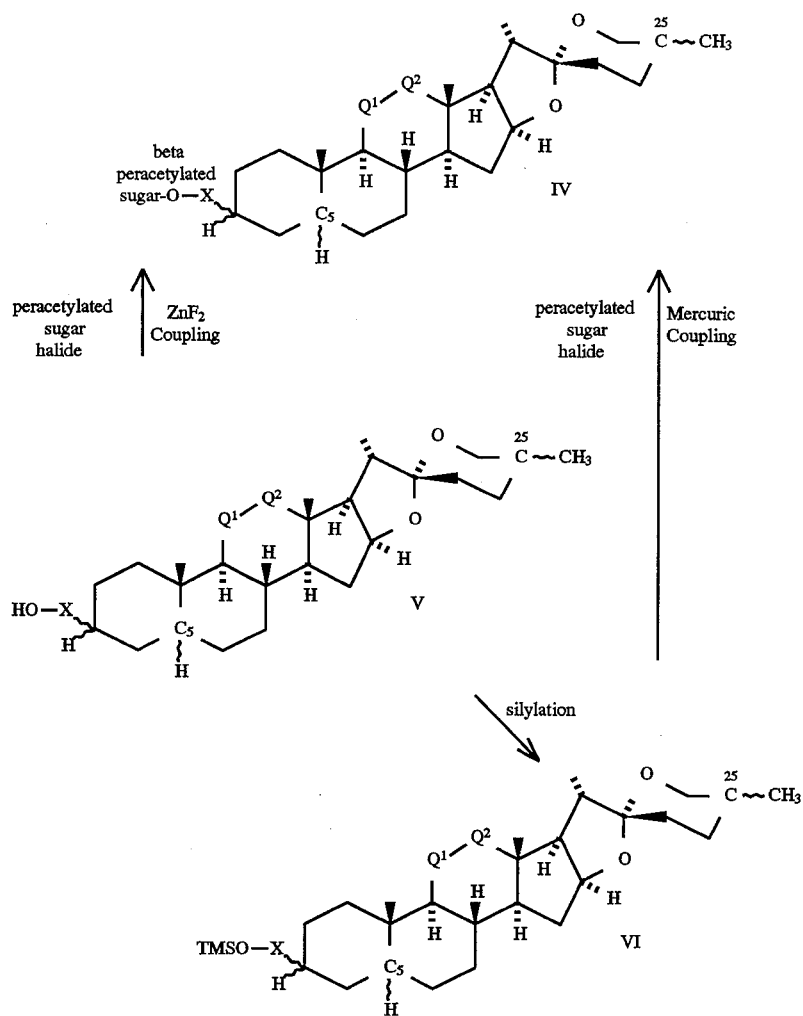

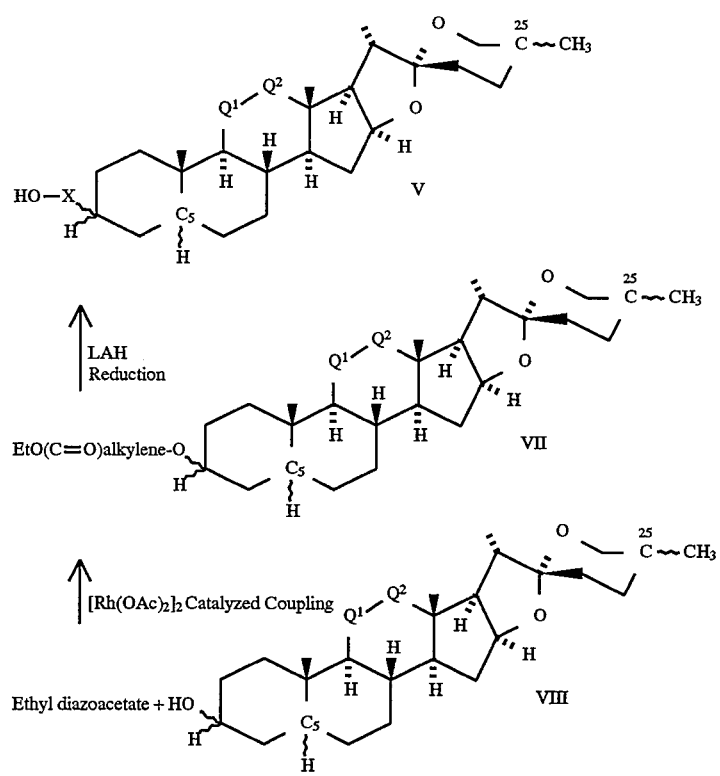
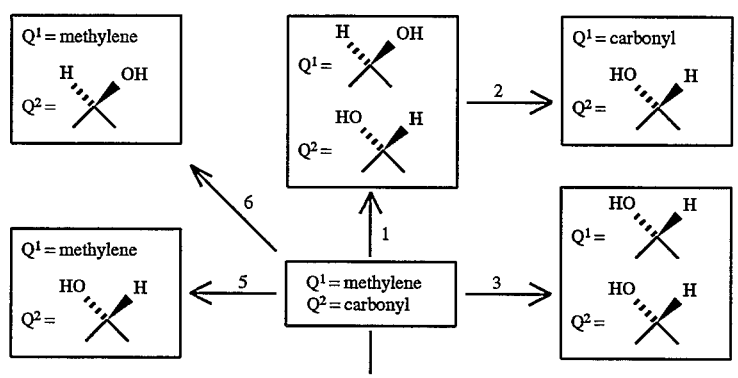

-continued
SCHEME IV
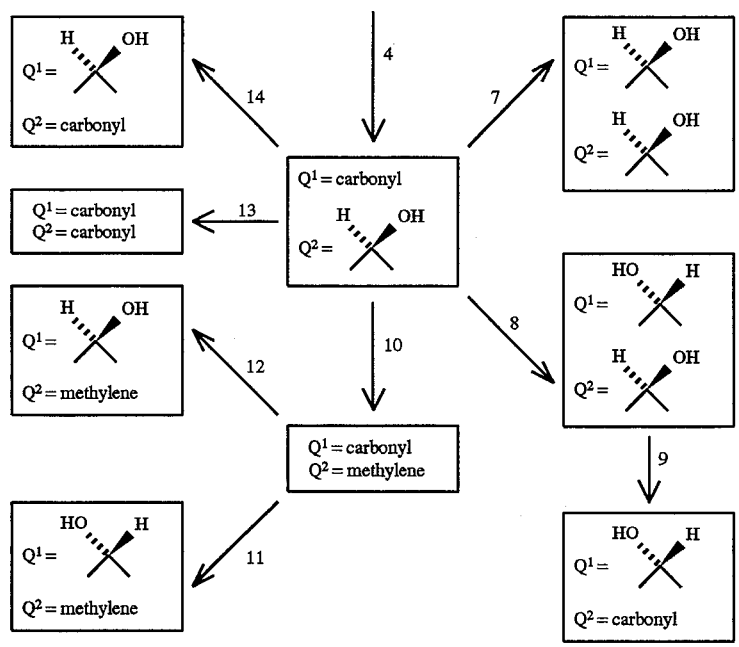
SCHEME V
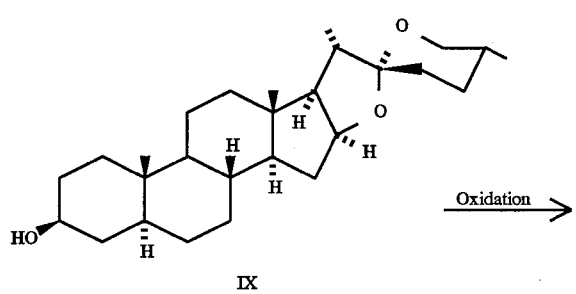
IX
Oxidation →
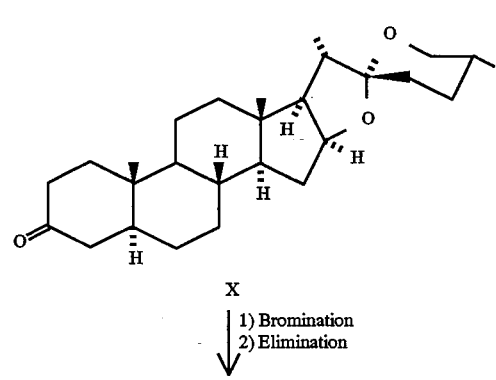
X
1) Bromination
2) Elimination
↓
-continued
SCHEME V
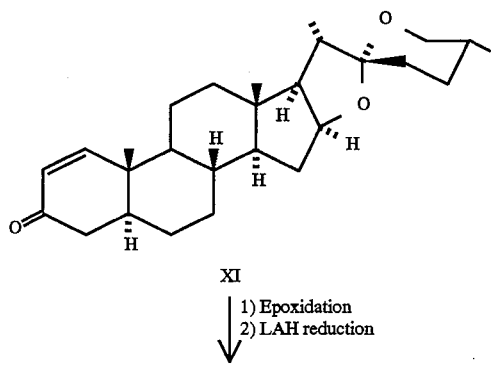
XI
1) Epoxidation
2) LAH reduction
↓
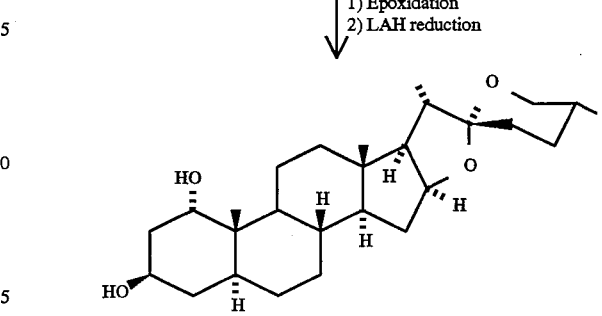
XII

SCHEME VI

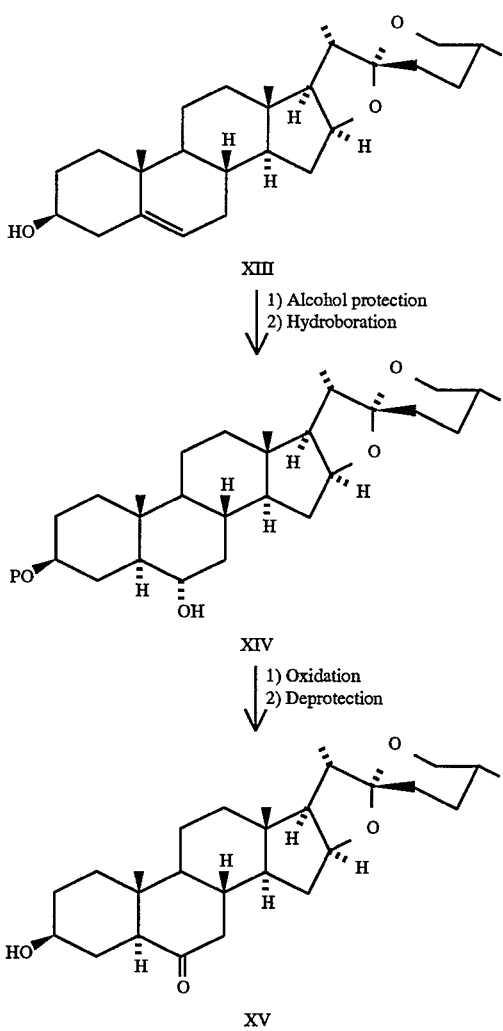

The Formula IA compounds are a subset of the Formula I compounds. Thus, in the following detailed descriptions of the invention (e.g., how to make the invention, how to use the invention) reference to the Formula I group of compounds, inherently encompasses the Formula IA compounds.

The following description of reaction Schemes I, II & III describe how to make the Formula I compounds wherein $Q^4$ and $Q^5$ are both methylene.

According to reaction Scheme I, the desired Formula I compounds wherein $Q^1$, $Q^2$ and $Q^3$ are as defined above may be prepared by deacetylating the appropriate alpha peracetylated Formula III compound or beta peracetylated Formula IV compound wherein $Q^1$ and $Q^2$ are as defined above and X is either a bond or alkylene—O—.

Typically the deacetylation is accomplished by combining the Formula III or IV compound with a nucleophilic base such as sodium methoxide or potassium cyanide in a solvent such as methanol, tetrahydrofuran, n-propanol or mixtures thereof at elevated temperatures of about 40° C. to about 100° C. (typically at reflux) and pressures of 0.5 psi to about 50 psi (typically ambient) for about 0.25 hour to about 2 hours. In addition, for Formula I compounds when the sugar is glucopyranuronosyl, the resultant deacetylated compound is further hydrolyzed by, for example, exposure to sodium hydroxide. Also, where appropriate, those compounds wherein either $Q^1$ or $Q^2$ are carbonyl may be reduced to yield the corresponding alcohols in an alternative process to performing the reduction prior to coupling (described in Reaction Scheme IV and the accompanying text). In an analogous manner, where appropriate, those compounds wherein either $Q^1$ or $Q^2$ are hydroxy may be oxidized to yield the corresponding carbonyl in an alternative process to performing the oxidation prior to coupling.

The desired Formula III compound wherein $Q^1$ and $Q^2$ are as defined above may be prepared by anomedzing the appropriate Formula IV compound wherein $Q^1$ and $Q^2$ are as defined above. The stereochemical terms alpha and beta refer to the configuration of the attachment carbon of the sugar.

Typically the anomedzation is performed by treatment with a mineral acid such as hydrobromic acid in an anhydrous aprotic solvent such as methylene chloride at temperatures of 20° C. to about 40° C. (typically ambient) for at least 24 hours, typically to several days. However, for arabanopyranosyl derivatives the alpha anomer is obtained directly from the saccharide-steroid coupling described below and the beta anomer from the above process (i.e., the nomenclature reverses).

According to Reaction Scheme II the desired Formula IV compounds wherein $Q^1$ and $Q^2$ are as defined above may be prepared by coupling the appropriate acetylated sugar halide (e.g., bromide) and steroid. More specifically, for those Formula IV compounds where the sugar is other than β-D-maltosyl, β-D-gentiobiosyl or β-D-2-acetamido-2-deoxy-glucopyranosyl, a zinc fluoride promoted coupling of the appropriate Formula V compound (wherein $Q^1$ and $Q^2$ are as defined above and X is either a bond or alkylene—O—) and peracetylated sugar halide is used and for those Formula IV compounds where the sugar is β-D-maltosyl, β-D-gentiobiosyl or β-D-2-acetamido-2-deoxy-glucopyranosyl, a mercuric bromide and mercuric cyanide promoted coupling of the appropriate Formula VI compound (e.g., trimethyl silyl ether of the Formula V compound wherein $Q^1$ and $Q^2$ are as defined above and X is either a bond or alkylene—O—) and peracetylated sugar halide is used.

Generally, the zinc fluoride promoted coupling of the Formula V compound and the peracetylated sugar bromide occurs in a non-protic, anhydrous reaction-inert solvent (e.g., acetonitrile) at a temperature of about 20° C. to about 100° C. for about 0.5 to about 12 hours. Typically about 0.5 to about 4 equivalents (based on Formula V compound) zinc fluoride is used and about 0.5 to about 3 equivalents acetylated sugar bromide is used. Preferably the coupling is acid catalyzed and it is especially preferred that hydrohalic acid generated during the reaction is used as the acid catalyst. The desired compounds may be prepared at pressures of 0.5 to 50 psi, although typically ambient pressures are used. In a preferred isolation technique the glycosides may be precipitated from the crude filtered reaction mixture (e.g., acetonitrile product solution) by the addition of about 25% to 75% water and the remainder alcohol (e.g., methanol). Precipitation of the product from aqueous methanol/acetonitrile requires less processing than an extractive isolation, and provides a product of greater purity.

Generally, the mercuric bromide and mercuric cyanide promoted coupling of the Formula VI compound and the acetylated sugar bromide is performed in an aprotic, anhydrous solvent such as methylene chloride at a temperature of about 20° C. to about 100° C. for about 0.5 to about 6 hours.

Typically about 0.5 to about 4 equivalents (based on Formula IV compound) mercuric bromide and mercuric cyanide is used and about 0.5 to about 3 equivalents peracetylated sugar bromide (e.g., β-D-maltosyl, β-D-gentiobiosyl or β-D-2-acetamido-2-deoxy-glucopyranosyl) is used. The desired compounds may be prepared at pressures of 0.5 to 50 psi, although typically ambient pressures are used. Preferably they are isolated as described for the zinc fluoride promoted coupling of the Formula V compound above.

The desired Formula VI compounds wherein Q and $Q^2$ are as defined above and X is either a bond or alkylene—O— may be prepared by silylating the appropriate Formula V compound wherein $Q^1$ and $Q^2$ are as defined above and X is either a bond or alkylene—O—.

Generally the Formula V compound, a base such as triethylamine and an activated trialkylsilyl compound (e.g., trimethylsilyl trifluoromethane sulfonate or trimethylsilyl chloride) are reacted in an aprotic, anhydrous solvent such as methylene chloride at a temperature less than about 10° C. for about 0.5 hour to about 2 hours.

According to Reaction Scheme III the desired Formula V compounds wherein $Q^1$ and $Q^2$ are as defined above and X is alkylene—O—may be prepared by reducing the appropriate Formula VII compound wherein $Q^1$ and $Q^2$ are as defined above.

Generally the reduction is performed by reaction of the Formula VII compound with lithium aluminum hydride in an anhydrous solvent such as tetrahydrofuran at temperatures of less than about 10° C. for about 0.5 hour to about 3 hours.

The desired Formula VII compounds wherein $Q^1$ and $Q^2$ are as defined above may be prepared by coupling the appropriate Formula VIII compound where $Q^1$ and $Q^2$ are as defined above with ethyl diazoacetate in the presence of rhodium acetate dimer. Thus, the Formula VIII compound and ethyl diazoacetate are reacted in an aprotic solvent such as methylene chloride in the presence of rhodium acetate dimer at ambient temperature for about 0.5 hour to about 3 hours.

The starting materials for the above described reaction schemes (e.g., ethyl diazoacetate, peracetylated sugar halides) are readily available or can be easily synthesized by those skilled in the art using conventional methods of organic synthesis.

In addition, as an aid to the preparation of the above steroids, the following paragraphs describe the preparation of the various Formula VIII compounds. Literature references for the preparation of Formula VIII steroid compounds (wherein $Q^1$ is methylene and $Q^2$ and the stereochemistry of the $C_5$ hydrogen and $C_{25}$ carbon are as defined below) are described in Table I.

TABLE I

Formula VIII Compounds Where $Q^1$ is Methylene and the $C_3$ Hydroxy Group is Beta

| $C_5$ hydrogen | $C_{25}$ | $Q^2$ | Reference |
|---|---|---|---|
| α | R | $CH_2$ | R. E. Marker et. al., J. Am. Chem. Soc.(1943) 65 1199. |
| α | R | C=O | Marker et. al., J. Am. Chem. Soc. (1947) 69, 2167. |
| α | S | $CH_2$ | Goodson & Noller J. Am. Chem. Soc. (1939) 61, 2420. |
| α | S | C=O | Callow & James J. Chem. Soc. (1955) 1671. |
| β | R | $CH_2$ | Marker et. al., J. Am. Chem. Soc. (1943) 65, 1199. |
| β | R | C=O | Marker et. al., J. Am. Chem. Soc. (1947) 69, 2167. |
| β | S | $CH_2$ | Marker et. al., J. Am. Chem. Soc. (1943) 65, 1199. |
| β | S | C=O | Kenney & Wall J. Org. Chem. (1957) 22, 468. |

The following paragraphs describe and/or give literature references for the preparation of the various steroids used as starting materials (i.e., the alternative stereochemistry at the $C_3$ position and the oxygenation and different epimers at $C_{11}$ and $C_{12}$) from the above Formula VIII compounds described in Table I. In general the preparation of the different oxygenated steroids is independent of the stereochemistry at the $C_3$, $C_5$ and $C_{25}$ positions. Thus, once the appropriate stereochemistry at the $C_3$, $C_5$ and $C_{25}$ positions are achieved where $Q^1$ and $Q^2$ are each methylene or where $Q^1$ is methylene and $Q^2$ is carbonyl, the various oxygenated compounds at $Q^1$ and $Q^2$ may be prepared therefrom.

Some of the preparation methods described herein will require protection of remote functionality (i.e., $Q^1$, $Q^2$ and $Q^3$). The need for these protecting groups will vary depending on the nature of the remote functionality and the conditions of the preparation methods. This need is readily determined by one skilled in the art. For a general description of protecting groups and their use, see T. W. Greene, Protective Groups in Organic Synthesis, John Wiley & Sons, New York, 1981.

The Formula VIII compounds wherein $Q^1$ is methylene, $Q^2$ is either methylene or carbonyl and the $C_3$ hydroxy is beta may be converted to the corresponding Formula VIII compounds where the $C_3$ hydroxy is alpha by the following two procedures. These preparative methods may be used independent of the $C_{25}$ stereochemistry.

If $Q^2$ is carbonyl, the carbonyl is protected as a ketal (e.g., ethylene ketal), by reacting the steroid with ethylene glycol and an acid catalyst according to the procedure of Engel and Rakhit, Can. J. Chem, 40, 2153, 1962. When the $C_5$ hydrogen is alpha, the $C_3$ hydroxy group is oxidized to the ketone using pyridinium chloro chromate (PCC) in methylene chloride at ambient conditions. Then the $C_3$ ketone is reduced with a sterically hindered reducing agent such as K-Selectride® reducing agent, at low temperature in tetrahydrofuran to give the $C_3$ alpha alcohol according to Gondos and Orr, *J. Chem. Soc. Chem. Commun.* 21, 1239, 1982. If appropriate, the $Q^2$ protecting group is removed with acid, such as hydrochloric acid, in an appropriate solvent such as acetone.

For those compounds wherein the $C_5$ hydrogen is beta the same procedures are used as were used when the $C_5$ hydrogen is alpha except the $C_3$ ketone is reduced using sodium borohydride in ethanol to famish the $C_3$ alpha alcohol.

Reaction Scheme IV illustrates the reaction pathways to achieve the Formula VIII compounds wherein $Q^1$ and $Q^2$ are defined above starting from the Formula VIII compound wherein $Q^1$ is methylene and $Q^2$ is carbonyl.

In general, preparation methods for these compounds may be found in L. F. Fieser and M. Fieser, Steroids, Reinhold Pub. Corp., New York, 1959 and references therein, however, the following descriptive text (which is keyed to Reaction Scheme IV) provides specific guidance.

Briefly according to Reaction Scheme IV method 1, the starting material is acetylated and brominated according to the procedure described in *J. Chem. Soc.*, 1956, 4344. This intermediate is then reduced with lithium aluminum hydride and treated with silver oxide by a procedure similar to that described in *Helv. Act. Chim,*, 1953, 36, 1241, The resulting β–11,12-epoxide is opened with trichloroacetic acid, saponified and reduced with zinc and acetic acid using the procedure described in *J. Chem. Soc.* 1956, 4330 to give the product shown for method 1.

In method 2, the starting material is selectively acetylated using the procedure described in *J. Chem. Sec.*, 1956,430. Using the procedure described in *Org. Syn.*, 1976, 55, 84, the resulting product is oxidized with chromium trioxide and pyridine. Using the procedure described in *Synthesis*, 1973, 790, the resulting product is saponified with potassium cyanide in water, methanol and THF to give the product shown for method 2.

In method 3, the starting material is converted to the corresponding toluenesulfonylhydrazone which is in turn treated with sodium methoxide using a procedure similar to that described in *J. Am. Chem. Soc.*, 1954, 76, 4013. The resulting 11-ene product is oxidized with osmium tetroxide and N-methylmorpholine-N-oxide according to the procedure describe in *Tetrahedron Letters*, 1976, 1973 to give the product shown for method 3.

In method 4, the starting material is monobrominated using a procedure described in U.S. Pat. No. 3,178,418, Hydrolysis of this intermediate using the procedure described in *J. Chem. Soc.* 1956, 4330 gives the product shown for method 4.

In methods 5 and 6, the starting material is reduced with lithium aluminum hydride according to the procedure described in *J. Am. Chem. Soc.*, 1954, 76, 4013. The two products shown in methods 5 and 6 are separated chromatographically.

In method 7, the starting material is reduced with lithium aluminum hydride according to the procedure described in *J. Am. Chem. Soc.*, 1951, 73, 1777 to give the product shown.

In method 8, the starting material is reduced with lithium and ammonia according to the procedure described in *J. Am. Chem. Soc.*, 1953, 75, 1282 to give the product shown.

In method 9, the starting material is acetylated according to the procedure described in *J. Am. Chem. Soc.*, 1955, 77, 1632 to give a mixture of acetates from which the 3,11-diacetate can be isolated. The unprotected 12-alcohol is then oxidized with chromium trioxide and pyridine according to the procedure described in *Org. Syn.*, 1976, 5–5, 84. Saponification of the acetates gives the product shown for method 9.

In method 10, the starting material is diacetylated using the procedure described in *J. Chem. Soc.* 1956, 4330. The diacetate is reduced with calcium and ammonia using the procedure described in *J. Chem. Soc.* 1956, 4334 to give the product shown for method 10.

In method 11, the starting material is reduced with lithium and ammonia according to the procedure described in *J. Am. Chem. Soc.*, 1953, 75, 1282 to give the product shown.

In method 12, the starting material is reduced with lithium aluminum hydride according to the procedure described in *J. Am. Chem. Soc.*, 1951, 73, 1777 to give the product shown.

In method 13, the starting material is selectively protected at the 3-alcohol with t-butyldimethylchlorosilane and imidazole using the procedure described in *J. Am. Chem. Soc.*, 1972, 94, 6190. Using the procedure described in *Org. Syn.*, 1976, 55, 84, the product is oxidized with chromium trioxide and pyridine. The 3-alcohol is then desilylated with hydrofluoric acid in acetonitrile using the procedure described in *J. Am. Chem. Soc.*, 1972, 94, 6190 to give the product shown for method 13.

In method 14, the starting material is selectively protected at the 3-alcohol with t-butyldimethylchlorosilane and imidazole using the procedure described in *J. Am. Chem. Soc.*, 1972, 94, 6190. The resulting intermediate is reduced with lithium aluminum hydride using the procedure described in *J. Am. Chem. Soc.*, 1951, 73, 1777. The resulting intermediate is selectively acetylated on the 12-alcohol, silylated on the 11-alcohol with trimethylsilyltriflate and 2,6-lutidine using the procedure described in *Tetrahedron Letters*, 1981, 22, 3455, and then deacetylated at the 12-alcohol with lithium aluminum hydride and an aqueous ammonium chloride quench. The 12-alcohol is oxidized with chromium trioxide and pyridine in methylene chloride using the procedure described in *Org. Syn.*, 1976, 55, 84, and then desilylated with hydrofluoric acid in acetonitrile using the procedure described in *J. Am. Chem. Soc.*, 1972, 94, 6190 to give the product shown in method 14.

According to Reaction Scheme V the desired Formula IA compounds wherein $Q^1$, $Q^2$, $Q^3$, $Q^4$, $Q^5$, $C_5$ and $C_{25}$ are as described in (E) above (i.e., oxygenated at the $Q^4$ position) may be prepared by the following procedures.

The desired Formula X compound can be prepared by the oxidation of tigogenin IX. Generally the oxidation is performed by reaction of tigogenin with pyridinium chlorochromate in a reaction inert solvent such as methylene chloride at 0° C. to ambient temperature for about 2 hours to about 10 hours.

The desired Formula XI compound can be prepared by bromination of the Formula X compound followed by an elimination reaction. Typically the bromination is performed by reaction of the Formula X compound with bromine in tetrahydrofuran at a temperature of about −78° C., followed by warming to ambient temperature for about 1 hour to about 3 hours. The elimination reaction is performed by reaction of the brominated product prepared above with lithium bromide and lithium carbonate in a polar, aprotic solvent such as dimethyl formamide at a temperature of about 100° C. to about 140° C. for about 1 hour to about 4 hours.

The desired Formula XII compound can be prepared by epoxidation of the appropriate Formula XI compound followed by lithium aluminum hydride reduction. Generally the epoxidation is performed by reaction of the Formula XI compound with hydrogen peroxide and sodium hydroxide in a polar, protic solvent such as methanol at ambient temperature for about 2 hours to about 6 hours. The reduction is performed by reaction of the epoxide prepared above with lithium aluminum hydride in a reaction inert solvent such as tetrahydrofuran at ambient temperature for 2 hours to about 6 hours.

The desired Formula IA compound as described in (E) above wherein $Q^4$ contains a hydroxy group may then be prepared from the appropriate Formula XII compound by a zinc fluoride catalyzed coupling followed by deacetylation with sodium methoxide as described previously. Those compounds wherein $Q^4$ is carbonyl may be prepared in an analogous manner, with the addition of oxidation with pyridinium chlorochromate (as described for Formula X compounds) prior to the deacetylation.

According to Reaction Scheme VI, the desired Formula IA compounds wherein $Q^1, Q^2, Q^3, Q^4 Q^5, C_5$ and $C_{25}$ are as described in (F) above (i.e., oxygenated at the $Q^5$ position) may be prepared by the following procedures.

The desired Formula (XIV) compound can be obtained by protection (as denoted by P) of the alcohol function in diosgenin (XIII) followed by hydroboration of the olefin. Typically, the alcohol is protected as an ethoxymethyl ether by reaction of diosgenin with ethoxymethyl chloride and diisopropylethyl amine in an anhydrous solvent such as methylene chloride at ambient temperature for about 2 hours to 6 hours. The hydroboration is performed by reaction of the compound prepared above with borane-tetrahydrofuran complex in a reaction-inert solvent such as tetrahydrofuran at ambient temperature for about 1 hour to about 6 hours.

The desired Formula XV compound can be prepared by oxidation of the appropriate Formula XIV compound followed by removal of the alcohol protecting group. Generally, the oxidation is performed by reaction of the Formula XIV compound with pyridinium chlorochromate in an anhydrous solvent such as methylene chloride at ambient temperature for about 2 hours to about 8 hours. The removal of the alcohol protecting group can be accomplished by reaction of the oxidized product prepared above with concentrated hydrochloric acid in a mixed solvent containing methanol and tetrahydrofuran at a temperature of about 40° C. to about 65° C. for about 5 minutes to about 1 hour.

The desired Formula IA compound as described in (F) above wherein $Q^5$ is carbonyl may then be prepared from the appropriate Formula XV compound by a zinc fluoride catalyzed coupling reaction followed by deacetylation using sodium methoxide as described previously. Those compounds where in $Q^5$ contain a hydroxy group may be prepared in an analogous manner with the addition of reduction prior to deacetylation. Typically the reduction is performed by reaction with sodium borohydride in a mixed solvent of ethanol and dichloromethane at ambient temperature for about 1 hour to about 6 hours.

The compounds of Formula I which have been obtained and have asymmetric carbon atoms can be separated into their diastereomers on the basis of their physical chemical differences by methods known per se., for example, by chromatography and/or fractional crystallization.

The compounds of this invention where the sugar is β-D-glucopyranuronosyl are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, many of the compounds of this invention may be isolated as hydrates.

The compounds of this invention are potent inhibitors of cholesterol absorption and thus are all adapted to therapeutic use as hypercholesterolemia controlling agents in mammals, particularly humans. Since hypercholesterolemia is closely related to the development of generalized cardiovascular, cerebral vascular or peripheral vascular disorders, secondarily these compounds prevent the development of atherosclerosis particularly arteriosclerosis.

The hypercholesterolemia controlling activity of these compounds may be demonstrated by methods based on standard procedures. For example, the in vivo activity of these compounds in inhibiting intestinal absorption of cholesterol may be determined by the procedure of Melchoir and Harwell (J. Lipid Res., 1985, 26, 306–315).

Activity can be determined by the amount of hypocholesterolemic agent that reduces the cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day the animals are fasted for 18 hours, then administered a 1.5 ml oral bolus of water containing 0.25% methylcellulose, 0.6% Tween 80 and 10% ethanol (control animals) or an oral bolus that contains, in addition, the desired concentration of the compound to be tested. Immediately following bolus administration, the animals receive a second 1.5 ml oral bolus of liquid hamster diet containing 1% [$^3$H] cholesterol (2.0 µCi/animal; 210 dpm/mol) and 0.5% cholic acid, and are fasted for an additional 24 hours. At the end of this second fasting period animals are sacrificed livers are excised, saponified and aliquots are decolorized by addition of hydrogen peroxide, and assessed for radioactivity. Total hepatic radioactivity is calculated based on measured liver weights. The degree of cholesterol absorption is expressed as a percentage of the total radioactivity administered as an oral bolus that is present in the liver 24 hours following bolus administration.

Anti-atherosclerosis effects of the compounds can be determined by the mount of agent that reduces the lipid deposition in the rabbit aorta. Male New Zealand white rabbits are fed a diet containing 0.4% cholesterol and 5% peanut oil for 1 week (meal-fed once a day). After 1 week, the rabbits are dosed daily with the desired concentration of the compound to be tested. After 8.5 weeks, drug treatment is discontinued and the animals are maintained on the cholesterol containing diet for an additional 2 weeks and then switched to a cholesterol free diet for 5 weeks. The animals are sacrificed, and the aortas removed from the thoracic arch to the branch of the iliacs. The aortas are cleaned of adventitia, opened longitudinally and then stained with Sudan IV as described by Holman et al. (Lab. Invet. 1958, 7, 42–47). The percent of the surface area stained is quantitated by densitometry using an Optimas Image Analyzing System (Image Processing Systems). Reduced lipid deposition is indicated by a reduction in the percent surface area stained in the drug treated group in comparison with the control rabbits.

Administration of the compounds of this invention can be via any method which delivers the compounds to the intestinal lumen. These methods include oral routes, intraduodenal routes etc.

The amount of steroidal glycoside administered will, of course, be dependent on the subject being treated, on the severity of the affliction, on the manner of administration and on the judgement of the prescribing physician. However, an effective dosage is in the range of 0.71 to 200 mg/kg/day, preferably 2 to 50 mg/kg/day, most preferably 2 to 7 mg/kg/day. For an average 70 kg human, this would amount to 0.05 to 14 g/day, preferably 0.14 to 3.5 g/day, most preferably 0.14 to 0.5 g/day.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an mount effective to alleviate the signs of the subject being treated, i.e., hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see Remington's Pharmaceutical Sciences., Mack Publishing Company, Easter, Pa., 15th Edition (1975).

EXAMPLE 1

(3β,5α,12β,25R)-3-(β-D-galactosyl)oxy]-12-hydroxyspirostane

Reduction of Ketones

To a room temperature solution of (3β,5α,25R)-3-[(β-D-galactosyl)oxy]-spirostan-12-one (1.33 g, 2.24 mmol; obtained via deacetylation of (3β,5α,25R)-3-[(tetraacetyl-β-D-galactosyl)oxy]spirostan-12-one (preparation B2) according to the procedure described in Example 3), ethanol (130 mL) and chloroform (260 mL) was added a solution of sodium borohydride (0.51 g, 13.4 mmol) and ethanol(50 mL). After stirring for 4 hours, methanol (200 mL) was added and stirring was resumed for 2 hours. The reaction mixture was concentrated in vacuo to give 3.38 g of crude product. Recrystailization from a mixture of methanol (80 mL) and water (8 mL), followed by washing with cold methanol (20 mL) and drying gave 1.33 g (quantitative yield) of the title compounds. MS: 595 (M+H). MP: >200° C. High resolution FAB MS (m/e): calc. for $C_{33}H_{55}O_9$: 595.3846, found: 595.3861.

The title compound was prepared from the appropriate starting material in an analogous manner using the procedure of Example 1.

EXAMPLE 2

(3β,5α,12β,25R)-3-[(β-D-cellobiosyl)oxy]-12-hydroxyspirostane

| m.p. | M.S. | | |
|---|---|---|---|
| >200° C. | 757(M + H) 779 (M + Na) | FAB HRMS (m/e): | calc. for $C_{39}H_{64}O_{14}Na$: 779.4194 found: 779.4250 |

EXAMPLE 3

(3β,5α,25R)-3-[(β-D-cellobiosyl)oxy]spirostan-11-one

Deacetylation

A mixture of (3β,5α,25R)-3-[(heptaacetyl-β-D-cellobiosyl)oxy]spirostan-11-one (6.57 g, 6.26 mmol), sodium methoxide (68 mg, 1.25 mmol), methanol (35 mL) and tetrahydrofuran (75 mL) was heated to reflux for 1 hour, followed by stirring at room temperature for 12 hours. A white precipitate formed within 30 minutes. The final suspension was concentrated in vacuo to give 6.0 g of crude product. This material was purified by flash chromatography (eluent: chloroform followed by 8:2 chloroform:methanol) to give 2.71 g (57% yield) of the title compound.

$^1$H NMR (DMSO-$d_6$) δ:5.22 (d, J=5 Hz, 1H); 5.00 (m, 3H); 4.64 (s, 1H); 4.58 (t, J=5 Hz, 1H); 4.54 (t, J=6 Hz, 1H); 4.34 (q, J=8 Hz, 1H); 4.27 (d, J=8 Hz, 1H); 4.23 (d, J=8 Hz, 1H); 3.68 –2.94 (m, 15 H); 2.34 (m, 2H); 2.08–0.81 (m, 23H); 0.92 (s, 3H); 0.86 (d, J=7 Hz, 3H); 0.72 (d, J=6 Hz, 3H); 0.59 (s, 3H). DEPT $^{13}$C NMR (DMSO-$d_6$) δ: 210.4 (s), 108.8 (s), 103.6 (d), 100.6 (d), 81.1 (d), 80.6 (d), 77.2 (d), 76.9 (d), 76.5 (d), 75.5 (d), 75.1 (d), 73.7 (d), 73.6 (d), 70.5 (d), 66.4 (t), 63.5 (d), 61.5 (t), 60.9 (t), 50.5 (d), 57.1(t), 54.7 (d), 44.3 (s), 44.1 (d), 41.7 (d), 36.8 (d), 35.6 (t), 35.2 (s), 34.0 (t), 32.6 (t), 31.3 (s), 30.2 (d), 29.2 (t), 28.9 (t), 28.2 (t), 17.5 (q), 17.3 (q), 14.8 (q), 12.3 (q). IR (KBr): 3407 (s), 1700 (m) $cm^{-1}$. High resolution FAB MS (m/e): calculated for $C_{39}H_{62}O_{14}Na$ 777.4037, found 777.4108. Analysis: calc. for $C_{39}H_{62}O_{14} \cdot 2H_2O$, C 59.22 H 8.41; found C 59.48, H 8.48. MP: >300° C.

A monohydrate crystalline form of the above titled product was prepared as follows:

A mixture of 20 g of the crude product prepared according to the above procedure, 600 ml of n-propanol, and 400 ml of water was stirred and heated to reflux. To the resulting solution was charged 2.0 g of diatomaceous earth. While still at reflux the insolubles were removed by filtration. The flitrate was atmospherically distilled to a total volume of 600 ml and cooled to ambient temperature. The resulting suspension was granulated for one hour and the product was collected by filtration. The undried recrystallized cake from the above recrystallization was suspended in 500 ml of methanol. This suspension was heated to reflux for 16 hours, cooled to ambient temperature, granulated for 48 hours, and isolated by filtration. Vacuum drying yielded 16.1 g (81% recovery) of the crystal monohydrate of the Example 3 titled compound.

EXAMPLES 4–47

The following compounds were prepared from the appropriate starting material in an analogous manner using the above procedures.

| Example # | Compound Name m.p. | M.S. | formula | elemental analysis |
|---|---|---|---|---|
| 4.) | (3β, 5α, 25R)-3-[(β-D-cellobiosyl)oxy]spirostan-12-one | | | |
| | >200° C. | 755 (M + H) | $C_{39}H_{62}O_{14}$· | calc. C 59.22; H 8.41 |
| | | 777 (M + Na) | 2 $H_2O$ | found C 59.54; H 8.64 |
| 5.) | (3α, 5α, 25R)-3-[(β-D-cellobiosyl)oxy]spirostane | | | |
| | >300° C. | 741 (M + H) | $C_{39}H_{64}O_{13}$· | calc. C 62.46; H 8.74 |
| | | | 0.5 $H_2O$ | found C 62.31; H 8.36 |
| 6.) | (3β, 5β, 25R)-3-[(β-D-cellobiosyl)oxy]spirostane | | | |
| | >300° C. | 741 (M + H) | $C_{37}H_{64}O_{13}$· | calc. C 61.72; H 8.77 |
| | | | $H_2O$ | found C 61.76; H 9.04 |
| 7.) | (3β, 5α, 25R)-3-[(β-D-glucuronosyl)oxy]spirostane | | | |
| | >200° C. | 615 (M + Na) | FAB HRMS (m/e): | calc. for $C_{33}H_{51}O_9Na_2$ 637.3278 |
| | | 637 (M + 2 Na) | | found 637.3329 |
| 8.) | (3β, 5α, 25R)-3-[(β-D-glucosyl)oxy]spirostan-12-one | | | |
| | >200° C. | 593 (M + H) | $C_{33}H_{52}O_9$· | calc. C 64.89; H 8.91 |
| | | 615 (M + Na) | $H_2O$ | found C 64.46; H 8.62 |
| 9.) | (3β, 5α, 25R)-3-[(β-D-galactosyl)oxy]spirostan-11-one | | | |
| | >200° C. | 593 (M + H) | $C_{33}H_{52}O_9$· | calc. C 65.38; H 8.89 |
| | | 615 (M + Na) | 0.75 $H_2O$ | found C 65.34; H 8.63 |
| 10.) | (3β, 5β, 25S)-3-[(β-D-cellobiosyl)oxy]spirostane | | | |
| | >250° C. | 741 (M + H) | $C_{39}H_{64}O_{13}$· | calc. C 60.99; H 8.85 |
| | | | 1.5 $H_2O$ | found C 60.69; H 8.90 |
| 11.) | (3β, 5α, 25R)-3-[(β-D-cellobiosyl)oxyethoxy)spirostane | | | |
| | >250° C. | 785(M + H) | $C_{41}H_{68}O_{14}$· | calc. C 60.65; H 8.81 |
| | | | 1.5 $H_2O$ | found C 60.53; H 8.97 |
| 12.) | (3β, 5α, 25R)-3-[(β-D-galactopyranosyl)oxy]ethoxy)spirostane | | | |
| | 225° C. | 623(M + H) | $C_{35}H_{58}O_8$· | calc. C 65.14; H 9.45 |
| | (dec) | | 1.25 $H_2O$ | found C 65.39; H 9.61 |
| 13.) | (3β, 5α, 25R)-3-[(β-D-maltosyl)oxy]spirostane | | | |
| | 230° C. | 741 (M + H) | $C_{39}H_{64}O_{13}$· | calc. C 60.30; H 8.82 |
| | (dec) | | 2 $H_2O$ | found C 60.64; H 8.84 |
| 14.) | (3β, 5α, 25R)-3-[(β-D-lactosyl)oxy]spirostane | | | |
| | >260° C. | 741 (M + H) | $C_{39}H_{64}O_{13}$ | calc. C 63.22; H 8.71 |
| | | | | found C 6296; H 8.65 |
| 15.) | (3β, 5α, 25R)-3-[(β-D-lactosyl)oxy]spirostan-12-one | | | |
| | >260° C. | 755(M + H) | $C_{39}H_{62}O_{14}$· | calc. C 61.31; H 8.31 |
| | | | 0.5 $H_2O$ | found C 61.02; H 8.45 |
| 16.) | (3β, 5α, 25R)-3-[(β-D-2-acetamido-2-deoxyglucopyranosyl)oxy]-spirostane | | | |
| | 210–212° C. | 620(M + H) | $C_{39}H_{62}O_{14}$· | calc. C 65.91; H 9.32; N 2.20 |
| | | | 1.0 $H_2O$ | found C 66.07; H 9.55; N 2.26 |
| 17.) | (3β, 5α, 25R)-3-[(α-D-gentiobiosyl)oxy]spirostane | | | |
| | 265° C. | 741 (M + H) | $C_{39}H_{64}O_{13}$· | calc. C 61.72; H 8.77 |
| | (dec) | | 1.0 $H_2O$ | found C 61.71; H 8.96 |
| 18.) | (3β, 5α, 25R)-3-[(α-L-arabanopyranosyl)oxy]spirostane | | | |
| | >200° C. | 549(M + H) | $C_{32}H_{52}O_7$· | calc. C 68.36; H 9.59 |
| | | | 0.75 $H_2O$ | found C 68.30; H 9.64 |
| 19.) | (3β, 5α, 25R)-3-[(α-D-arabanopyranosyl)oxy]spirostane | | | |
| | >200° C. | 549(M + H) | $C_{32}H_{52}O_7$· | calc. C 65.73; H 9.65 |
| | | | 2.0 $H_2O$ | found C 65.54; H 9.25 |
| 20.) | (3β, 5α, 25R)-3-[(β-L-xylopyranosyl)oxy]spirostane | | | |
| | >230° C. | 549(M + H) | $C_{32}H_{52}O_7$· | calc. C 68.91; H 9.58 |
| | | | 0.5 $H_2O$ | found C 68.52; H 9.36 |
| 21.) | (3β, 5α, 25R)-3-[(β-L-fucopyranosyl)oxy]spirostane | | | |
| | >230° C. | 561(M + H) | $C_{33}H_{54}O_7$· | calc. C 68.25; H 9.72 |
| | | | 1.0 $H_2O$ | found C 68.62; H 9.53 |
| 22.) | (3β, 5α, 25R)-3-[(β-D-xylopranosyl)oxy]spirostane | | | |
| | >220° C. | 549(M + H) | $C_{32}H_{52}O_7$· | calc. C 66.23; H 9.64 |
| | | | 1.75 $H_2O$ | found C 66.32; H 9.31 |
| 23.) | (3β, 5α, 25R)-3-[(β-D-fucopyranosyl)oxy]spirostane | | | |
| | >220° C. | 563(M + H) | $C_{33}H_{54}O_7$· | calc. C 69.32; H 9.69 |
| | | | 0.5 $H_2O$ | found C 69.32; H 9.78 |
| 24.) | (3β, 5α, 25R)-3-[(β-D-galactopyranosyl)oxy]spirostane | | | |
| | >200° C. | 579(M + H) | $C_{33}H_{54}O_8$· | calc. C 66.12; H 9.47 |
| | | | 1.25 $H_2O$ | found C 66.46; H 9.26 |
| 25.) | (3β, 5α, 25R)-3-[(3-O-β-D-galactopyranosyl)-α-D-arabanopyranosyl)oxy]spirostane | | | |
| | >200° C. | 579(M + H) | $C_{38}H_{62}O_{12}$· | calc. C 62.64; H 8.78 |
| | | | 1 $H_2O$ | found C 62.93; H 8.66 |

-continued

| Example # | Compound Name m.p. | M.S. | formula | elemental analysis |
|---|---|---|---|---|
| 26.) | (3β, 5α, 25S)-3-[(β-D-galactopyranosyl)oxy]spirostane >200° C. | 579(M + H) | $C_{33}H_{54}O_8 \cdot$ 2 $H_2O$ | calc. C 64.51; H 9.44 found C 64.69; H 9.41 |
| 27.) | (3β, 5α, 25R)-3-[(α-D-cellobiosyl)oxy]spirostan-11-one 290–292° C. | 777(M + Na) | FAB HRMS (m/e): | calc. for $C_{39}H_{62}O_{14}$ 755.4218 found 755.4163 |
| 28.) | (3β, 5α, 12β, 25R)-3-[(β-D-cellobiosyl)oxy]-12-hydroxyspirostane-11-one >200° C. | 771(M + H) 793(M + Na) | $C_{39}H_{62}O_{15} \cdot$ $H_2O$ | calc. C 60.76; H 8.10 found C 61.76; H 8.88 |
| 29.) | (3β, 5α, 11α, 25R)-3-[(β-D-cellobiosyl)oxy]-11-hydroxyspirostane >210° C. | 779(M + Na) | FAB HRMS (m/e): | calc. for $C_{39}H_{64}O_{14}Na$ 779.4194 found 779.4138 |
| 30.) | (3β, 5α, 11β, 25R)-3-[(β-D-cellobiosyl)oxy]-11-hydroxyspirostane >210° C. | 779(M + Na) | $C_{39}H_{64}O_{14} \cdot$ $H_2O$ | calc. C 60.45; H 8.28 found C 60.41; H 8.58 |
| 31.) | (3β, 5α, 25R)-3-[(β-D-glucopyranosyl)oxy]spirostan-11-one 293–295° C. | 593(M + H) | $C_{33}H_{52}O_9 \cdot$ 2 $H_2O$ | calc. C 64.89; H 8.91 found C 64.48; H 8.85 |
| 32.) | (3β, 5α, 11β, 12β, 25R)-3-[(β-D-cellobiosyl)oxy]-11, 12-di(hydroxy)spirostane >230° C. | 773(M + H) | $C_{39}H_{64}O_{15} \cdot$ 2 $H_2O$ | calc. C 57.91; H 8.47 found C 57.87; H 8.41 |
| 33.) | (3β, 5α, 11α, 12β, 25R)-3-[(β-D-cellobiosyl)oxy]-11, 12-di(hydroxy)spirostane >230° C. | 773(M + H) | $C_{39}H_{64}O_{15} \cdot$ 1 $H_2O$ | calc. C 59.22; H 8.41 found C 59.27; H 8.32 |
| 34.) | (3β, 5α, 12α, 25R)-3-[(β-D-cellobiosyl)oxy]-12-hydroxyspirostane >230° C. | 757(M + Na) | $C_{39}H_{64}O_{14} \cdot$ 3 $H_2O$ | calc. C 57.76; H 8.70 found C 57.56; H 8.61 |
| 35.) | (3β, 5α, 25R)-3-[(β-D-lactosyl)oxy]spirostan-11-one >270° C. | 755(M + H) | $C_{39}H_{62}O_{14}$ | calc. C 62.05; H 8.28 found C 61.88; H 8.14 |
| 36.) | (3β, 5α, 11α, 12α, 25R)-3-[(β-D-cellobiosyl)oxy]-11, 12-di(hydroxy)spirostane 287–288° C. | 795(M + H) | FAB HRMS (m/e): | calc. for $C_{39}H_{64}O_{15}Na$ 795.4143 found 795.4164 |
| 37.) | (3β, 5α, 11α, 25R)-3-[(β-D-cellobiosyl)oxy]-11-hydroxyspirostan-12-one >300° C. | 771(M + H) 793(M + Na) | $C_{39}H_{62}O_{15} \cdot$ 2.5 $H_2O$ | calc. C 57.41; H 8.28 found C 57.38; H 7.90 |
| 38.) | (3β, 5α, 25R)-3-[(β-D-cellobiosyl)oxy]spirostan-11, 12-dione 244–246° C. | 769(M + H) 791(M + Na) | $C_{39}H_{60}O_{15} \cdot$ 4 $H_2O$ | calc. C 55.70; H 8.15 found C 55.93; H 7.99 |
| 39.) | (3β, 5α, 11β, 12α, 25R)-3-[(β-D-cellobiosyl)oxy]-11, 12-di(hydroxy)spirostane >228–229° C. | 773(M + H) 795(M + Na) | FAB HRMS (m/e): | calc. for $C_{39}H_{64}O_{15}Na$ 795.41429 found 795.4164 |
| 40.) | (3β, 5α, 12α, 25R)-3-[(β-D-cellobiosyl)oxy]-12-hydroxyspirostan-11-one >230° C. | 771(M + H) 793(M + Na) | $C_{39}H_{62}O_{15} \cdot$ 3 $H_2O$ | calc. C 56.78; H 8.31 found C 56.97; H 7.80 |
| 41.) | (3β, 5α, 12β, 25R)-3-[(β-D-lactosyl)oxy]-12-hydroxyspirostan-11-one >275° C. | 771(M + H) | $C_{39}H_{62}O_{15} \cdot$ 0.5 $H_2O$ | calc. C 60.06; H 8.14 found C 59.92; H 7.89 |
| 42.) | (3β, 5α, 25R)-3-[(β-D-maltotriosyl)oxy]spirostan-11-one >230° C. | 939(M + Na) | $C_{39}H_{62}O_{15} \cdot$ 4.5 $H_2O$ | calc. C 54.15; H 8.17 found C 54.08; H 7.84 |
| 43.) | (3β, 5α, 25R)-3-[(β-D-maltosyl)oxy]spirostan-11-one >280° C. | 755(M + H) | $C_{39}H_{62}O_{14} \cdot$ 2 $H_2O$ | calc. C 59.22; H 8.41 found C 59.38, H 8.13 |
| 44.) | (1α, 3β, 5α, 25R)-3-[(β-D-cellobiosyl)oxy]-1-hydroxyspirostane >280° C. | 757(M + H) | $C_{39}H_{64}O_{14} \cdot$ $H_2O$ | calc. C 60.45; H 8.58 found C 60.30; H 8.21 |
| 45.) | (3β, 5α, 25R)-3-[(β-D-cellobiosyl)oxy]spirostan-1-one >250° C. | 755(M + H) | $C_{39}H_{62}O_{14} \cdot$ 1.2 $H_2O$ | calc. C 60.32; H 8.36 found C 60.24; H 8.13 |
| 46.) | (3β, 5α, 25R)-3-[(β-D-cellobiosyl)oxy]spirostan-6-one >200° C. | 754(M + H) | FAB HMRS (m/e): | calc. for $C_{39}H_{62}O_{14}$ 755.4286 found 755.4219 |
| 47.) | (3β, 5α, 6α, 25R)-3-[(β-D-cellobiosyl)oxy]-6-hydroxyspirostane >250° C. | 756(M + H) | $C_{39}H_{64}O_{14} \cdot$ 2 $H_2O$ | calc. C 59.12; H 8.65 found C 59.23; H 8.46 |

EXAMPLE 48

(3β,5α,11β,25R)-3-[(β-D-cellobiosyl)oxy]-11-hydroxyspirostan-12-one

Deacetylation

Based on the procedure described in *Synthesis*, 1973, 790, (3β,5α,11β,25R)-3-[(heptaacetyl-β-D-cellobiosyl)oxy]spirostan-11-ol-12-one (240 mg, 0.225 mmol) was dissolved in methanol (20 mL) and tetrahydrofuran (10 mL). To this solution was added a solution of potassium cyanide (146 mL, 2.25 mmol) in water (0.1 mL) and methanol (5 mL). The resulting mixture was heated to 80° C. for four hours. After cooling, the mixture was concentrated to dryness and purified by flash chromatography (9:1 chloroform:methanol eluent) to give the title compound. Mp 245°–247° C. MS (m/e): 771 (P+1), 793 (P+Na). Analysis: calc for $C_{39}H_{62}O_{15} \cdot 3H_2O$, C 56.70, H 8.31; found, C 56.97, H 7.80.

PREPARATION A1

(3β,5α,25R)-3-[(Heptaacetyl-α-D-cellobiosyl)oxy]spirostan-11-one

Anomerization

Hydrobromic acid (30% in acetic acid, 1.2 mL) was added to a room temperature solution of (3β, 5α, 25R)-3-[(heptaacetyl-β-D-cellobiosyl)-oxy]spirostan-11-one (2.0 g) in methylene chloride (35 mL) and the resulting mixture was stirred at room temperature for 94 hours. The reaction was quenched by slow addition of saturated aqueous sodium bicarbonate (20 mL). The organic layer was separated, dried over magnesium sulfate, and dried in vacuo to give 1.637 g of a black solid. Purification by repeated flash chromatography (1:1 hexane:ethyl acetate eluent) provided 651 mg (33% yield) of the title compound.

$^1$H NMR (CDCl$_3$) δ: 5.41 (t, J=10 Hz, 1H); 509 (complex, 3H); 4.91 (t, J=8 Hz, 1H); 4.69 (dd, J=4 & 10 Hz, 1H); 4.49 (complex, 3H); 4.36 (dd, J=4 & 13 Hz, 1H); 3.99 (m, 3H); 3.67 (m, 2H); 3.40 (m, 3H); 2.45 (m, 1H); 2.22 (s, 2H); 2.11 (s, 3H); 2.07 (s, 3H); 2.03 (s, 6H); 2.00 (s, 3H); 1.99 (s, 3H); 1.97 (s, 3H); 2.00–0.80 (m, 22H); 1.02 (s, 3H); 0.92 (d, J=7 Hz,3H); 0.77 (d, J=7 Hz, 3H); 0.69 (s, 3H). DEPT $^{13}$C NMR (CDCl$_3$) δ: 210.0 (s), 170.5 (s), 170.3 (s), 170.2 (s), 169.6 (s), 169.3 (s), 169.1 (s), 109.2 (s), 100.9 (d), 94.3 (d), 80.6 (d), 78.0 (d), 77.0 (d), 73.1 (d), 71.9 (d), 71.8 (d), 71.2 (d), 69.6 (d), 68.1 (d), 67.8 (d), 66.9 (d), 64.4 (d), 62.0 (t), 61.5 (t), 60.7 (d), 57.6 (t), 55.7 (d), 45.0 (d), 44.3 (s), 41.8 (d), 36.9 (d), 35.5 (t), 35.4 (t), 35.1 (s), 32.7 (t), 31.3 (t), 31.2 (t), 30.2 (d), 28.7 (t), 28.0 (t), 27.4 (t), 20.9 (q), 20.7 (q), 20.6 (q), 20.5 (q), 17.1 (q), 17.0 (q), 14.2 (q), 12.1 (q). IR (Kbr): 1751 (s), 1706 (m) cm$^{-1}$. MS (m/e): 1049 (M+H), 1071 (M +Na). Analysis: calc. for $C_{53}H_{76}O_{21} \cdot H_2O$, C 59.65 H 7.37; found C 59.66 H 7.00. MP: 248°–249° C.

PREPARATION B1

(3β,5α,25R)-3-[(Heptaacetyl-β-D-cellobiosyl)oxy]spirostane-11-one

Zinc Fluoride Promoted Coupling of Free Spirostane

A suspension of (3β,5α,25R)-3-hydroxyspirostan-11-one (3.0 g, 6.97 mmol) and anhydrous zinc fluoride (2.88 g, 27.9 mmol) in dry acetonitrile (175 mL) was dried by removal of 75 mL of acetonitrile by distillation. The suspension was allowed to cool, heptaacetyl-β-D-cellobiosyl bromide (9.75 g, 13.9 mmol) was added and the resulting suspension was heated to 65° C. for 3 hours. After cooling to room temperature, methylene chloride (150 mL) was added, the suspension was stirred for 10 minutes and filtered. The filtrate was concentrated in vacuo to give 10 g of crude product. This material was dissolved in 8:2 chloroform:methanol, preadsorbed on silica gel and purified by flash chromatography (eluent: 1:1 ethyl acetate:hexane followed by pure ethyl acetate) to give 6.81 g (93% yield) of the title material.

$^1$H NMR (CDCl$_3$) δ: 5:11 (complex, 2 H); 5.04 (t, J=9 Hz, 1H); 4.90 (t, J=9 Hz, 1H); 4.83 (t, J=8 Hz, 1H); 4.49 (complex, 4H); 4.34 (dd, J=4.5 & 12.5 Hz, 1H); 4.04 (t, J=13 Hz, 1H); 4.03 (t, J=11 Hz, 1H); 3.72 (t, J=9.5 Hz, 1H); 3.65 (m, 1H); 3.56 (m, 1H); 3.45 (m, 1H); 2.47 (m, 1H); 2.22 (s, 2H); 2.08 (s, 3H); 2.06 (s, 3H); 2.00 (s, 6H); 1.99 (s, 6H); 1.96 (s, 3H); 2.00–1.00 (m, 22H); 0.98 (s, 3H); 0.92 (d, J=7 Hz, 3H); 0.77 (d, J=7 Hz, 3H); 0.68 (s, 3H). DEPT$^{13}$C NMR (CDCl$_3$) δ: 209.9 (s), 170.5 (s), 170.3 (s), 170.2 (s), 169.9 (s), 169.8 (s), 169.5 (s), 169.3 (s), 169.0 (s), 109.2 (s), 100.8 (d), 99.4 (d), 90.0 (s), 80.6 (d), 79.4 (d), 76.6 (d), 75.3 (s), 72.9 (d), 72.6 (d), 72.5 (d), 71.9 (d), 71.8 (d), 71.6 (d), 67.8 (s), 66.9 (t), 64.4 (d), 62.1 (t), 61.5 (t), 60.8 (s), 60.7 (d), 57.6 (t), 55.7 (d), 44.8 (d), 44.3 (s), 41.8 (d), 36.9 (d), 35.6 (t), 35.2 (s), 34.1 (t), 32.7 (t), 31.3 (t), 31.2 (t), 30.2 (d), 29.0 (t), 28.7 (t), 28.0 (t), 20.9 (q), 20.7 (q), 20.6 (q), 20.5 (q), 20.5 (q), 17.1 (q), 17.0 (q), 14.2 (q), 12.0 (q). IR (KBr): 1756 (s), 1706 (m) cm$^{-1}$. MS (m/e): 1049 (M+H). Analysis: calc. for $C_{53}H_{76}O_{21} \cdot H_2O$, C 59.65, H 7.37; found C 59.86, H 7.25. MP: 210°–212° C.

In an analogous manner the following compounds, Preparation B2–B31, were prepared from the appropriate starting material using the above general procedure.

PREPARATION 2

(3β,5α,25R)-3-[(tetraacetyl-β-D-galactosyl)oxy]spirostane-12-one

PREPARATION B3

(3β,5α,25R)-3-[(heptaacetyl-β-D-cellobiosyl)oxy]spirostane

PREPARATION B4

(3β,5α,25R)-3-[(heptaacetyl-β-D-cellobiosyl)oxy]spirostane

PREPARATION B5

(3β,5α,25R)-3-[(triacetyl-β-D-glucuronosyl)oxy]spirostane methyl ester

PREPARATION B6

(3β,5α,25R)-3-[(tetraacetyl-β-D-glucopyranosyl)oxy]spirostane-12-one

PREPARATION B7

(3β,5α,25R)-3-[(tetraacetyl-β-D-galactopyranosyl)oxy]spirostane-11-one

PREPARATION B8

(3β,5α,25R)-3-[(heptaacetyl-β-D-cellobiosyl)oxy]spirostane

PREPARATION B9

(3β,5α,25R)-3-([(heptaacetyl-β-D-cellobiosyl)oxy]
ethoxy)spirostane

PREPARATION B10

(3β,5α,25R)-3-([(tetraacetyl-β-D-galactopyranosyl)
oxy]ethoxy)spirostane

PREPARATION B11

(3β,5α,25R)-3-[(heptaacetyl-β-D-lactosyl)oxy]
spirostane

PREPARATION B12

(3β,5α,25R)-3-[(heptaacetyl-β-D-lactosyl)oxy]
spirostane-12-one

PREPARATION B13

(3β,5α,25R)-3-[(triacetyl-α-L-arabanopvranosyl)
oxy]spirostane

PREPARATION B14

(3β,5α,25R)-3-[(triacetyl-α-D-arabanopyranosyl)
oxy]spirostane

PREPARATION B15

(3β,5α,25R)-3-[(triacetyl-β-L-xylopyranosyl)oxy]
spirostane

PREPARATION B16

(3β,5α,25R)-3-[(triacetyl-β-L-fucopyranosyl)oxy]
spirostane

PREPARATION B17

(3β,5α,25R)-3-[(triacetyl-β-D-xylopyranosyl)oxy]
spirostane

PREPARATION B18

(3β,5α,25R)-3-[(triacetyl-β-D-fucopyranosyl)oxy]
spirostane

PREPARATION B19

(3β,5α,25R)-3-[(tetraacetyl-β-D-galactopyranosyl)
oxy]spirostane

PREPARATION B20

(3β,5α,25R)-3-[(hexaacetyl-3-0-β-D-
galactopyranosyl]-α-D-arabanopyranosyl)oxyl-
spirostane

PREPARATION B21

(3β,5α,25S)-3-[(tetraacetyl-β-D-galactopyranosyl)
oxy]spirostane

PREPARATION B22

(3β,5α,12β,25R)-3-[(heptaacetyl-β-D-cellobiosyl)
oxy]-12-hydroxyspirostan-11-one

PREPARATION B23

(3β,5α,11α,25R)-3-[(heptaacetyl-β-D-cellobiosyl)
oxy]-11-hydroxyspirostate

PREPARATION B24

(3β,5α,11β,25R)-3- [(heptaacetyl-β-D-cellobiosyl)
oxy]-11-hydroxyspirostane

PREPARATION B25

(3β,5α,25R)-3-[(tetraacetyl-β-D-glucopyranosyl)
oxy]spirostan-11-one

PREPARATION B26

(3β,5α,11β,12β,25R)-3-[(heptaacetyl-β-D-
cellobiosyl)oxy]-11, 12-hydroxy)spirostane

PREPARATION B27

(3β,5α,25R)-3-[(heptaacetyl-β-D-cellobiosyl)oxy]-
11, 12-di(hydroxy)spirostane

PREPARATION B28

(3β,5α,25R)-3-[heptaacetyl-β-D-cellobiosyl)oxy]
12-hydroxyspirostane

PREPARATION B29

(3β,5α,25R)-3-[(heptaacetyl-β-D-lactosyl)oxy]
spirostan-11-one

PREPARATION B30

(3β,5α,25R)-3-[(heptaacetyl-β-D-cellobiosyl)oxy]
spirostan-12-one

PREPARATION B31

(3β,5α,11α,12α,25R)-3-[(heptaacetyl-β-D-
cellobiosyl)oxy]-11,12-dihydrospirostane

PREPARATION B32

(3β,5α,11α,25R,)-3-[(heptaacetyl-β-D-cellobiosyl)
oxy]-11-hydroxyspirostan-12-one

PREPARATION B33

(3β,5α,25R)-3-[(heptaacetyl-β-D-cellobiosyl)oxy]
spirostan-11,12-dione

PREPARATION B34

(3β,5α,11β,12α,25R)-3-[(heptaacetyl-β-D-
cellobiosyl)oxy]-11,12-di(hydroxy)spirostane

PREPARATION B35

(3β,5α,12α,25R)-3-[(β-D-cellobiosyl)oxy]-12-
hydroxyspirostan-11-one

PREPARATION B36

(3β,5α,25R)-3-[(heptaacetyl-β-D-lactosyl)oxy]-12-
hydoxyspirostan-11

PREPARATION B37

(3β,5α,25R)-3-[(dodecaacetyl-β-D-maltotriosyl)oxy]spirostan-11-one

PREPARATION B38

(3β,5α,25R)-3[(heptaacetyl-β-D-maltosyl)oxy]spirostan-11-one

PREPARATION B39

(1α,3β,5α,25R)-3,[(heptaacetyl-β-D-cellobiosyl)oxy]-1-hydroxyspirostane

PREPARATION B40

(3β,5α,25R)-3-[(heptaacetyl-β-D-cellobiosyl)oxy]spirostan-6-one

PREPARATION B41

(3β,5α,11β,25R)-3-[(heptaacetyl-β-D-cellobiosyl)oxy]-11-hydroxyspirostan-12-one

PREPARATION C1

(3β,5α,25R)-3-([(heptaacetyl-β-D-lactosyl)oxy]spirostane

Mercuric Bromide/Mercuric Cyanide Promoted Coupling of Silylated Spirostane

Powdered 4A molecular sieves (1 g) were added to a solution of trimethylsilyl tigogenin (1.17 g, 2.4 mmol) and acetobromo lactose (3.36 g, 4.8 mmol) in $CH_2Cl_2$ (15 mL) and $CH_3CN$ (5 mL) at room temperature. After stirring for 15 minutes $Hg(CN)_2$ (2.4 g, 9.6 mmol) and $HgBr_2$ (3.4 g, 9.6 mmol) were added and the mixture stirred at room temperature for three hours. The mixture was diluted with ethyl acetate (50 mL) and filtered. The flitrate was washed with 1N HCl(3 ×30 mL) and brine (1 ×30 mL), dried ($Na_2SO_4$) filtered and concentrated in vacuo. The product was purified by flash chromatography (10–20% EtOAc/$CH_2Cl_2$) to afford 400 mg product as a colorless solid. MS 489 (M+H)$^+$.

$^1$H NMR (250 MHz, $CDCl_3$) δ5.35 (d, 1H, J=1.0 Hz); 5.2 (dd, 1H, J=4.5, 4.5 Hz); 5.15 (dd, 1H, J=6.0, 5.0 Hz); 4.95 (dd, 1H, J=4.5, 1.0 Hz); 4.85 (dd, 1H, J=5.0, 4.5 Hz); 4.55 (d, 1H, J=6.0 Hz); 4.4 (m, 3H); 4.1 (m, 3H); 3.85 (t, 1H, J=3.0 Hz); 3.8 (t, 1H, J=4.5 Hz); 3.5 (m, 3H); 3.35 (t, 1H, J=5.0 Hz); 2.15 (s, 3H); 2.12 (s, 3H); 2.07 (s, 12H); 2.0 (s, 3H); 2.0–0.5 (m, 27H); 0.98 (d, 3H, J=4.0 Hz); 0.82 (s, 3H); 0.8 (d, 3H, J=4.0 Hz); 0.73 (s, 3H).

In an analogous manner the following compounds, preparations C2–C4, were prepared from the appropriate starting material using the above general procedure.

PREPARATION C2

(3β,5α,25R)-3-([(heptaacetyl-β-D-maltosyl)oxy]-spirostane

PREPARATION C3

(3β,5α,25R)-3-([(triaacetyl-β-D-2-acetamido-2-deoxyglucopyranosyl)oxy]-spirostane

PREPARATION C4

(3β,5α,25R)-3-([(heptaacetyl-β-D-gentiobiosyl)oxy]spirostane

PREPARATION D1

(3β,5α,25R)-3-trimethylsilyloxyspirostane

Silylation of Spirostanes

Trimethylsilyl trifluoromethanesulfonate (4 mL, 22.1 mmol) was added dropwise to a solution of tigogenin (6 g, 14.4 mmol) and triethyl amine (6 mL, 45 mmol) in $CH_2Cl_2$ (50 mL) at 0° C. After 1 hour, the mixture was diluted with ether (100 mL) and washed with saturated $NaHCO_3$ solution (2×50 mL) and brine (1×50 mL), dried ($Na_2SO_4$) filtered and concentrated in vacuo. Upon addition of methanol, a precipitate formed which was filtered and washed with methanol and dried to afford 6.2 g product as a colorless solid.

MP 197°–198° C. MS 489 (M+H)$^+$. $^1$H NMR (250 MHz, $CDCl_3$) δ4.35 (q, 1H, J=3.0 Hz); 3.5 (m, 2H); 3.4 (t, 1 H, J=5.5 Hz); 2.0–0.5 (m, 27H); 1.0 (d, 3H, J=4.0 Hz); 0.85 (s, 3H); 0.8 (d, 3H, J=4.0 Hz); 0.75 (s, 3H); 0.1 (s, 9H).

PREPARATION E1

(3β,5α,25R)-3-(2-hydroxyethoxy)-spirostane

LAH Reductions

Lithium aluminum hydride (0.285 g, 7.5 mmol) was added to a solution of tigogenin-O-acetic acid ethyl ester (2.5 g, 4.98 mmol) in THF (50 mL) at 0° C. After 1 hour, the reaction was quenched by the sequential addition of $H_2O$ (0.285 mL), 15% NaOH (0.285 mL) and $H_2O$ (0.85 mL). The mixture was diluted with ether (25 mL) and dried with $MgSO_4$, filtered and concentrated in vacuo to afford 2.1 g product as a colorless solid. MP 207°–208° C. MS 461 (M+H)$^+$.

$^1$H NMR (250 MHz, $CDCl_3$)δ4.4 (q, 1H, J=3.0 Hz); 3.7 (m, 2H); 3.6 (m, 2H); 3.5 (m, 1H); 3.4 (t, 1H, J=5.5 Hz); 3.3 (m, 1H); 2.0–0.5 (m, 28H, 1.0 (d, 3H, J=4.0 Hz); 0.85 (s, 3H); 0.8 (d, 3H, J=4.0 Hz); 0.75 (s, 3H).

PREPARATION F1

((3β,5α,25R)-spirostan-3-yl)-O-acetic acid ethyl ester

[Rh(OAc)$_2$]$_2$ Catalyzed Couplings

Ethyl diazoacetate (5.5 mL, 0.048 mol) dissolved in 30 mL of $CH_2Cl_2$ was added dropwise over 1 hour to a solution of tigogenin (10 g, 0.024 mol) and rhodium acetate dimer (250 mg) in $CH_2Cl_2$ (250 mL) at room temperature. Gas evolved throughout the addition and when the addition was complete the mixture stirred for an additional 1 hour. The mixture was diluted with hexanes (100 mL) and filtered through a plug of silica gel. The filtrate was concentrated in vacuo and upon addition of methanol to the residue, a precipitate formed which was filtered and washed with methanol and dried to afford 6.0 g product as a colorless solid. MP 119°–120° C. MS 503 (M+H)$^+$.

$^1$H NMR (250 MHz, $CDCl_3$) δ4.35 (q, 1H, J=3.0 Hz); 4.2 (m, 2H); 4.1 (s, 2H); 3.4 (m, 3H); 2.0–0.5 (m, 30H); 0.95 (d, 3H, J=4.0 Hz); 0.8 (s, 3H); 0.75 (d, 3H, J=4.0 Hz); 0.72 (s, 3H).

PREPARATION G1

(3β,5α,11α,12α,25R)-spirostan-3,11,12-triol (3β,5α,11α,25R)-11,23-dibromo-3-acetoxyspirostan-12-one The title compound was synthesized from (3β,5α,25R)-3-acetoxyspirostan-12-one according to the procedure described in *J. Chem. Soc.*, 1956, 4344.

(3β,5α11α,12β,25R)-11,23-dibromospirostan-3,12-diol (3β,5α,11α,25R)-11,23-dibromo-3-acetoxyspirostan-12-one (20.00 g, azeotropically dried with toluene) was dissolved in THF (600 mL) and cooled to −78° C. Lithium aluminum hydride (96.0 mL of 1.0M THF solution) was slowly added and the resulting mixture was stirred at −78° C. for 2 hours and 0° C. for 0.5 hour. Using a cannula, the mixture was cautiously transferred into stirred 3M aqueous ammonium chloride (200 mL). The organic phase was separated, combined with THF washes of the solid residues, and concentrated to give the title compound.

(3β,5α,11β,12β,25R)-23-bromo-11,12-epoxyspirostan-3-ol

The following procedure is a variation of that described in *Helv. Act. Chim.*, 1953, 36, 1241. ((3β,5α,11α,12β, 25R)-11,23-dibromospirostan-3,12-diol (18.08 g) was dissolved in pyridine (500 mL) at room temperature and treated with silver oxide (70.0 g). The resulting mixture was stirred in the dark for 71 hours. The mixture was filtered and the solid washed with ether and then chloroform. These washes were combined with the flitrate and concentrated. The resulting solid was purified by flash chromatography (1:1 hexane-:ethyl acetate) to give 12.2 g of a 1:1 mixture of the title compound and (3β,5α,25R)-23-bromospirostan-3-ol-12-one. Further chromatography (7:3 hexane:ethyl acetate) provides pure title. compound.

(3β,5α,11β,12α,25R)-23-bromo-12-(trichloroacetoxy)spirostan-3,11-diol

Using the procedure described in *J. Chem. Soc.*, 1956, 4330, (3β,5α,11β,12β,25R)-23-bromo-11,12-epoxyspirostan-3-ol was treated with trichloroacetic acid in toluene at room temperature for 3 days to give the title compound.

(3β,5α,11β,12α,25R)-23-bromo-spirostan-3,11,12-triol

Using the procedure described in *J. Chem. Soc.*, 1956, 4330, (3β,5α,11β,12α,25R)-23-bromo-12-(trichloroacetoxy)spirostan-3,11-diol was saponified with sodium hydroxide in water and ethanol to give the title compound.

(3β,5α,11β,12α,25R)-spirostan-3,11,12-triol

Using the procedure described in *J. Chem. Soc.*, 1956, 4330, (3β,5α,11β,12α,25R)-23-bromo-12-(trichloroacetoxy)-spirostan-3,11-diol was reduced with zinc and acetic acid to give the title compound.

PREPARATION G2

(3β,5α,12α,25R)spirostan-3,12-diol-11-one (3β,5α,11β,12α,25R)-3,12-di(acetoxy)spirostan-11-ol Using the procedure described in *J. Chem. Soc.*, 1956, 4330, (3β,5α,11β,12α,25R)-spirostan-3,11,12-triol (preparation G1) was selectively acetylated with acetic anhydride and pyridine to give the title compound.

(3β,5α,12α,25R)-3,12-di(acetoxy)spirostan-11-one

Using the procedure described in *Org. Syn.*, 1976, 55, 84, (3β,5α,11β,12α,25R)-3,12-di(acetoxy)-spirostan-11-ol was oxidized with chromium trioxide and pyridine in methylene chloride to give the title compound.

(3β,5α,12α,25R)-spirostan-3,12-diol-11-one

Using the procedure described in *Syn.*, 1973, 790, (3β, 5α,12α,25R)-3,12-di(acetoxy)spirostan-11-one was saponified with potassium cyanide in water, methanol and THF to give the title compound.

PREPARATION G3

(3β,5α,11β,25R)spirostan-3,11-diol (3β,5α,11β,25R)spirostan-3,11-diol (3β,5α,25R)spirostan-3-ol-11-one (Aldrich Chemical Company, Milwaukee, Wisc. or Steraloids Inc., Wilton, N.H., or see preparation G13) was converted into the title compound via reduction with lithium aluminum hydride in THF at room temperature according to the procedure described in *J. Am, Chem. Soc.*, 1951, 73, 1777.

PREPARATION G4

(3β,5α,11α,25R)spirostan-3,11-diol (3β,5α,11α,25R)spirostan-3,11-diol (3β,5α,25R)spirostan-3-ol-11-one (Aldrich Chemical Company, Milwaukee, Wisc. or Steraloids Inc., Wilton, N.H., or see preparation G13) was converted into the title compound via reduction with lithium and ammonia according to the procedure described in *J. Am. Chem. Soc.*, 1953, 75, 1282.

PREPARATION G5

(3β,5α,11β,12β,25R)spirostan-3,11,12-triol (3β,5α,11β,12β,25R)spirostan-3,11,12-triol (3β,5α,12β,25R)-3,12-di(acetoxy)spirostan-11-one (purchased from Steraloids, Inc., or see preparation G13) was converted into the title compound via reduction with lithium aluminum hydride in THF at room temperature according to the procedure described in *J. Am. Chem. Soc.*, 1951, 73, 1777.

PREPARATION G6

(3β,5α,11α,12β,25R)spirostan-3,11,12-triol (3β,5α,12β,25R)spirostan-3,12-diol-11-one (3β,5α,12β,25R)-3,12-di(acetoxy)spirostan-11-one (purchased from Steraloids, Inc., or see preparation G13) was saponified with potassium carbonate in water, methanol and THF to provide the title compound.

(3β,5α,11α,12β,25R)spirostan-3,11,12-triol (3β,5α,25R)spirostan-3,12-diol-11-one was converted into the title compound via reduction with lithium and ammonia according to the procedure described in *J. Am. Chem. Soc.*, 1953, 75, 1282.

PREPARATION G7

(3β,5α,12β,25R)spirostan-3,12-diol (3β,5α,12β,25R)spirostan-3,12-diol

Using the procedure described in *J. Am. Chem. Soc.*, 1954, 76, 4013, (3β,5α,25R)-spirostan-3-ol-12-one was reduced with lithium aluminum hydride in ether to give a mixture of C-12 alcohols from which the title compound was isolated.

PREPARATION G8

(3β,5α,25R)-spirostan-3-ol-11,12-dione

(3β,5α,12β,25R)-3-(t-butyldimethylsilyloxy)spirostan-12-ol-11-one

Using the procedure described in *J. Am. Chem. Soc.*, 1972, 94, 6190, (3β,5α,12β,25R)-spirostan-3,12-diol-11-one (see preparation G6) was silylated with t-butyldimethylchlorosilane and imidazole in DMF to give the title compound.

(3β,5α,25R)-3-(t-butyldimethylsilyloxy)spirostan-11,12-dione

Using the procedure described in *Org. Syn.*, 1976, 55, 84, (3β,5α,12β,25R)-3-(t-butyldimethyisilyloxy)-spirostan-12-ol-11-one was oxidized with chromium trioxide and pyridine in methylene chloride to give the title compound.

(3β,5α,25R)-spirostan-3-ol-11,12-dione

Using the procedure described in *J. Am. Chem. Soc.*, 1972, 94, 6190, (3β,5α,25R)-3-(t-butyldimethylsilyloxy) spirostan-11,12-dione was desilylated with hydrofluoric acid in acetonitrile to give the title compound.

PREPARATION G9

(3β,5α,11β,25R)-spirostan-3,11-diol-12-one

(3β,5α,11β,12β,25R)-3-(t-butyldimethylsilyloxy) spirostan-11,12-diol

(3β,5α,12β,25R)-3-(t-butyldimethylsilyloxy)spirostan-12-ol-11-one (see procedure G8) was converted into the title compound via reduction with lithium aluminum hydride in THF at room temperature according to the procedure described in *J. Am. Chem. Soc.*, 1951, 73, 1777.

(3β,5α,11β,12β,25R)-3-(t-butyldimethylsilyloxy)-12-acetoxyspirostan-11-ol

(3β,5α,11β,12β,25R)-3-(t-butyldimethylsilyloxy) spirostan-11,12-diol was selectively acetylated with acetic anhydride, pyridine and dimethylaminopydriine in methylene chloride to give the title compound.

(3β,5α,11β,12β,25R)-3-(t-butyldimethylsilyloxy)-11-(trimethylsilyloxy)-12- acetoxyspirostane

(3β,5α,11β,12β,25R)-3-(t-butyldimethylsilyloxy)-12-acetoxyspirostan-11-ol was silylated with trimethylsilyltriflate and 2,6-lutidine in methylene chloride according to the procedure described in *Tetrahedron Letters*, 1981, 22, 3455.

(3β,5α,11β,12β,25R)-3-(t-butyldimethylsilyloxy)-11-(trimethylsilyloxy)spirostan-12-ol

(3β,5α,11β,12β,25R)-3-(t-butyldimethylsilyloxy)-11-(trimethylsilyloxy)-12-acetoxyspirostane was deacetylated by treatment with lithium aluminum hydride in THF followed by catious addition aqueous ammonium chloride. The resulting title compound suffered 11 to 12 silyl group migration on silica gel, and thus had to used unpurified.

(3β,5α,11β,25R)-3-(t-butyldimethylsilyloxy)-11-(trimethylsilyloxy)spirostan-12-one

(3β,5α,11β,12β,25R)-3-(t-butyldimethylsilyloxy)-11-(trimethylsilyloxy)spirostan-12-ol was oxidized with chromium trioxide and pyridine in methylene chloride according to the procedure described in *Org. Syn.*, 1976, 55, 84 to give the title compound.

(3β,5α,11β,25R)-spirostan -3,11-diol-one

The title compound was synthesized from (3β,5α,11β, 25R)-3-(t-butyidimethylsilyloxy)-11-(trimethylsilyloxy) spirostan-12-one was desilylated with hydrofluoric acid in acetonitrile according to the procedure described in *J. Am. Chem. Soc.*, 1972, 94, 6190. The title compound must be carefully handled because it will rearrange to (3β,5α,12β, 25R)-spirostan-3,12-diol-11-one if exposed to base.

PREPARATION G10

(3β,5α,11α,25R)spirostan-3,11-diol-12-one

(3β,5α,11α,12β,25R)3,11-di(acetoxy)spirostan-12-ol

(3β,5α,11α,12β,25R)-spirostan-3,11,12-triol (see preparation G6)was acetylated according to the procedure described in *J. Am. Chem. Soc.*, 1955, 77, 1632 to give a mixture of acetates from which the title compound could be isolated.

(3β,5α,11α,25R)3,11-di(acetoxy)spirostan-12-one

(3β,5α,11α,12β,25R)3,11-di(acetoxy)spirostan-12-ol was oxidized with chromium trioxide and pyridine in methylene chloride according to the procedure described in *Org. Syn.*, 1976, 55, 84 to give the title compound.

(3β,5α,11α,25R)spirostan-3,11-diol-12-one (3β,5α,11α, 25R)-3,11-di(acetoxy)spirostan-12-one was saponified with sodium methoxide in methanol and THF to give the title compound.

PREPARATION G11

(3β,5α,11α,12α,25R)-spirostan-3,11,12-triol

(3β,5α,25R)spirostan-3-ol-12-tosylhydrazone

(3β,5α,25R)-spirostan-3-ol-12-one (8.00 g) was dissolved in glacial acetic acid (200 mL) and warmed to 50° C. Paratoluenesulfonylhydrazide (6.928 g) was added and the solution was stirred at 50° C. for 30 min. After an additional 2 hours of stirring at room temperature, water (200 mL) was added. The resulting solid was collected, washed with water (100 mL), dried, triturated with refluxing acetone (300 mL), filtered hot and dried to give 3.903 g of the title compound.

(3β,5α,25R)spirost-11-en-3-ol

A mixture of (3β,5α,25R)spirostan-3-ol-12-tosylhydrazone (9.100 g) and sodium methoxide (8.379 g) in DMF (200 mL) was heated to 150° C. for 35 minutes, then cooled to room temperature. The mixture was then poured into ice water (1200 mL) and the resulting suspension filtered. The collected solid was washed with water (100 mL), air-dried, and dissolved in methylene chloride (700 mL). This solution was washed with water (2×200 mL), dried with MgSO$_4$, and concentrated to give a white solid. Following flash chromatography, 2.384 g of the title compound (mp 179°–181° C., lit. 188°–192° C.- *J. Am. Chem. Soc.*, 1954, 76, 4013) was isolated.

(3β,5α,11α,12α,25R)spirostan-3,11,12-triol

(3β,5α,25R)spirost-11-en-3-ol was oxidized to the title compound with osmium tetroxide and N-methylmorpholine-N-oxide in water, t-butanol and acetone according to the procedure describe in *Tetrahedron Letters*, 1976, 1973.

PREPARATION G 12

(3β,5α,12β,25R)spirostan-3,12-diol-11-one (3β,5α, 11β,25R)-11-bromospirostan-3-ol-12-one A glass lined reactor was charged with 50 gallons of methanol then subsurface sparged with hydrochloric acid gas until 7.7 Kg (5.0 eq) were charged. Upon completion of this sparge, the reactor was charged with 18.8 Kg (42.2 mole) of (3β,5α,25R)spirostan-3-ol-12-one, 50 gallons of methanol and 10 gallons of methylene chloride. This mixture was cooled to 10° C. and a solution of 8.4 Kg bromine (52.7 mole, 1.25 eq) in 10 gallons of methylene chloride was added over 2 hours while a pot temperature of approximately 10° C. was maintained. Once the addition was complete the reaction was allowed to warm to room temperature and was stirred for 2 hours. TLC at this point indicated complete reaction.

The reaction was diluted with 50 gallons of water and stirred for 10 minutes. After separation of layers, the aqueous layer was extracted twice with 30 gallons of methylene chloride. The three combined organic extracts were washed twice with 30 gallons of water, once with 30 gallons of saturated brine, then dried using 7.0 Kg of magnesium sulfate. The drying agent was removed by filtration on a 30 inch Lapp followed by two 3 gallon methylene chloride washes. The filtrate and washes combined were atmospherically distilled to a 7 gallon total volume. Two 10 gallon methanol charges were made followed by continued distillation. When a final volume of <10 gallons had been reached the mixture was cooled to room temperature. The resulting suspension was granulated for 2 hours, filtered on a 30 inch Lapp, and the filter cake was washed twice with 3 gallons of methanol. Vacuum drying the filter cake at 45–50° C. yielded 12.6 Kg (58.6% yield) of the title compound.

($3\beta,5\alpha,12\beta,25R$)spirostan-3,12-diol-11-one

A glass lined reactor was charged with 12.4 Kg of ($3\beta,5\alpha,11\beta,25R$)-11-bromospirostan-3-ol-12-one (24.34 mole), 33 gallons of 33 gallons of water and 7.5 Kg (189 mole, 7.75 eq) of sodium hydroxide pellets. The reaction was heated to reflux over 1.5 hours, maintained at reflux for 4.5 hours (pot temperature was 83° C.), then cooled to room temperature. TLC at this point indicated complete reaction.

The reaction was distilled to remove the t-butanol. This was accomplished both by vacuum and atmospheric distillation. During the concentration two 32.5 gallon charges of water were added. Once the t-butanol had been removed, the aqueous suspension was cooled to room temperature and granulated for 2 hours. The suspension was filtered on a 30 inch Lapp, washed twice with 3 gallons of water, and the filter cake was air dried at 60 ° C. This afforded 11.1 Kg of the title compound.

PREPARATION G13

($3\beta,5\alpha,25R$)spirostan-3-ol-11-one ($3\beta,5\alpha,25R$)-3,12-diacetoxyspirostan-11-one A glass lined reactor was charged with 26 gallons of pyridine, 26 gallons of acetic anhydride and 11.0 Kg of ($3\beta,5\alpha,12\beta,25R$)spirostan-3,12-diol-11-one (preparation G12). This mixture was refluxed for 2 hours (pot temperature 128° C.) and allowed to cool to room temperature. The reaction was vacuum distilled to a total volume of 15 gallons (pot temperature approximately 45° C. during distillation). The suspension was diluted with 25 gallons of acetic acid and further vacuum distilled to a 15 gallon total volume (pot temperature at end approximately 80° C.). The mixture was diluted with 87 gallons of water and cooled to room temperature. After 5 hours of granulation, the titled compound was isolated by filtration on a 30 inch Lapp followed by two 3 gallon water washes. The filter cake was dried at 60° C. under vacuum to yield 12.2 Kg (93.3%).

($3\beta,5\alpha,25R$)spirostan-3-ol-11-one

A stainless steel reactor was cooled to −80° C. by passing liquid nitrogen through internal coils. Ammonia was added to the reactor until 54.5 Kg (80 liters, 3,200 mole, 170 eq) had been charged.

At the same time that the ammonia charge was commencing, a glass lined reactor was charged with 10.0 Kg of ($3\beta,5\alpha,12\beta,25R$)-3,12-diacetoxyspirostan-11-one 18.84 mole) and 40 gallons of THF. This solution was atmospherically distilled until a 26 gallon total volume had been reached.

At the completion of the ammonia charge, 2.8 Kg of calcium turnings (69.0 gram atoms, 3.7 eq) were added over 30 minutes while maintaining a pot temperature of −50° C. At the completion of this addition the THF solution of ($3\beta,5\alpha,25R$)-3, 12-diacetoxyspirostan-11-one was added over 20 minutes (pot temperature at the end of the addition was −35° C.) followed by a 1.0 gallon THF dnse. The reaction mixture was stirred for 30 minutes at −35° C. to −40° C. While the reaction was at −35° C. to −40° C., 3.33 liters of bromobenzene (4.98 Kg, 31.7 mole, 1.68 eq) were added followed by 3.33 liters of water.

After this addition, the distillation of ammonia from the reactor was initiated. This distillation was directed to a water scrubber. Once all of the ammonia had been removed, the reaction (now at 24° C.) was transferred to a glass lined reactor followed by a 4 gallon THF rinse. The solution and rinse combined were vacuum distilled to a thick oil. To this was added 35 gallons of methanol and 3.3 Kg (59 mole) of potassium hydroxide pellets. This mixture was heated at reflux for 1 hour, cooled, then 10 liters of acetic acid and 44 gallons of water were charged. This suspension was further cooled to room temperature and granulated for 1 hour. The titled compound was isolated by filtration on a 30 inch Lapp followed by a 5 gallon 3:1 water/methanol wash, Vacuum drying at 55° C. yielded 7.05 Kg (86.9%).

PREPARATION G: Physical Data

Satisfactory MS and IR data was obtained on all of the ($3\beta,5\alpha,25R$)spirostan-3-ols described in preparation G (see table 1). The various diol and triol products could be distinguished by proton NMR (see table 2)

TABLE 1

| | Diagnostic Mass Spectrometry and Infrared Data | | |
|---|---|---|---|
| compound | molecular formula | LSMIS parent ion (m/z) | IR diagnostic resonances (cm−1, intensity, solvent) |
| 11α-ol | $C_{27}H_{44}O_4$ | 433 | 3575 (m), 3440 (m) (CHCl$_3$) |
| 11β-ol | $C_{27}H_{44}O_4$ | 433 | 3560 (m), 3425 (m) (CHCl$_3$) |
| 12α-ol | $C_{27}H_{44}O_4$ | 433 | 3590 (m), 3420 (m) (CHCl$_3$) |
| 12β-ol | $C_{27}H_{44}O_4$ | 433 | — |
| 11α, 12α-diol | $C_{27}H_{44}O_5$ | 449 | 3424 (m) (KBr) |
| 11α, 12β-diol | $C_{27}H_{44}O_5$ | 449 | 3550 (m), 3450 (m) (CHCl$_3$) |
| 11β, 12α-diol | $C_{27}H_{44}O_5$ | 449 | 3441 (m) (KBr) |
| 11β, 12β-diol | $C_{27}H_{44}O_5$ | 449 | 3600 (m), 3450 (m) (CHCl$_3$) |
| 11α-ol-12-one | $C_{27}H_{42}O_5$ | 447 | 3515 (m), 1705 (s) (KBr) |
| 11β-ol-12-one | $C_{27}H_{42}O_5$ | 447 | 3450 (m), 1712 (s) (KBr) |
| 12α-ol-11-one | $C_{27}H_{42}O_5$ | 447 | 3410 (m), 1706 (s) (KBr) |

TABLE 1-continued

| | Diagnostic Mass Spectrometry and Infrared Data | | |
|---|---|---|---|
| compound | molecular formula | LSMIS parent ion (m/z) | IR diagnostic resonances (cm−1, intensity, solvent) |
| 12β-ol-11-one | $C_{27}H_{42}O_5$ | 447 | 3475 (m), 1708 (s) (CHCl$_3$) |
| 11, 12-dione | $C_{27}H_{40}O_5$ | 445 | 3600 (w), 3400 (m), 1710 (w) 1670 (s), 1605 (m) (CHCl$_3$)[1] |
| 11-one | $C_{27}H_{42}O_4$ | 431 | 3600 (w), 3450 (m), 1705 (s) (CHCl$_3$) |

[1]- IR data suggest that this compound readily tautomerizes enol ketone form in CHCl$_3$.

TABLE 2

| | Diagnostic Proton Nuclear Magnetic Resonance Data[2] |
|---|---|
| compound | peaks >2 ppm |
| 11α-ol | 3.90(ddd, 6, 6&4Hz, 1H), 2.26(dt, 13&4, 1H) |
| 11β-ol | 4.22(br s, 1H) |
| 12α-ol | 3.67(s, 1H), 2.37(dd, 8&7Hz, 1H) |
| 12β-ol | 3.26(dd, 10&4Hz, 1H) |
| 11α, 12α-diol | 3.91(m, 1H), 3.56(d, 3H, 1H), 2.45(dd, 9&7Hz, 1H) |
| 11α, 12β-diol | 3.55(m, 1H), 3.03(d, 8H, 1H), 2.21(dt, 12&4Hz, 1H) |
| 11β, 12α-diol | 4.12(br s, 1H), 3.55(d, 2Hz, 1H), 2.36(dd, 9&7Hz, 1H) |
| 11β, 12β-diol | 4.07(br s, 1H), 3.13(d, 3Hz, 1H) |
| 11α-ol-12-one | 3.72(m, 1H), 2.39(dt, 13&4Hz, 1H) |
| 11β-ol-12-one | 3.96(m, 1H), 2.2(m, 1H) |
| 12α-ol-11-one | 3.51(s, 1H), 2.57(dd, 8&7Hz, 1H), 2.2(complex, 7H) |
| 12β-ol-11-one | 3.78(s, 1H), 2.39(dt, 13&4Hz, 1H), 2.1(m, 2H) |

[2]- All samples run in CDCl$_3$ except 11β-ol-12-one which was run in DMSO-d$_6$. Peaks for $H_{16}$, $H_3$, $H_{26eq}$ and $H_{26ax}$ are also observed at >2 ppm. In CDCl$_3$, these are observed at 4.37(ddd, J = 9, 9&7Hz, 1H), 3.56(heptet, J = 4Hz, 1H), 3.45(ddd, J = 10, 6&2Hz, 1H), 3.35(t, J = 11Hz, 1H).

PREPARATION H1

(5α,25R)-spirostan-3-one

Pyridinium chlorochromate (PCC) was added to a mixture of tigogenin (50.00 g, 120.0 mmol), celite (160 g), in $CH_2Cl_2$ (1000 mL) at 0° C. The reaction was allowed to come to ambient temperature and was stirred for 5 hours. The reaction was diluted with 1000 4 mL Et$_2$O and was filtered through a silica gel plug. The plug was washed with an additional 6000 mL Et$_2$O. The filtrate was concentrated in vacuo to afford 45.00 g of the title compound (90.4%).
$^1$HNMR (250 MHz, CDCl$_3$) d 4.38 (q, J=7 Hz, 1H); 3.40 (m, 2H); 2.20–2.45 (m, 3H); 0.70–2.14 (m, 36H); 1.02 (s, 3H); 0.96 (d, J=7 Hz, 3H); 0.76 (s,3H);0.76 (d, J=7 Hz, 3H). MS: 415 (M+H)$^+$; MP 209°–211° C.

PREPARATION H2

(2α,5α,25R)-2-bromospirostan-3-one

A mixture of (5α,25R)-spirostan-3-one (1.00 g, 2.41 mmol) and tetrahydrofuran (10 mL) was cooled to −78° C. under nitrogen atmosphere. Bromine was added (0.39 g, 2.41 mmol) and the reaction mixture was gradually warmed to room temperature. After three hours, the reaction was quenched by the addition of saturated sodium bisulfite solution. The mixture was diluted with ethyl acetate, washed with saturated sodium bisulfite solution (1x), saturated sodium bicarbonate (1x), brine (1x), dried (sodium surfate), filtered, and concentrated in vacuo. Upon addition of ether, a precipitate formed which was filtered and washed with hexanes to give 1.20 g, (85%) of the title compound.
$^1$HNMR (250 MHz, CDCl$_3$) d 4.75 (q, J=7 Hz, 1H); 4.40 (q, J=7 Hz, 1H; 3.40 (m, 2H); 2.64 (q, J=6, 1H); 2.40 (m, 2H); 0.70–2.55 (m, 34H); 1.10 (s, 3H); 0.96 (d, J=7 Hz, 3H); 0.80 (s, 3H); 0.80 (d, J=7, 3H). MS 493 (M+H)$^+$.

PREPARATION H3

(5α,25R)-spirost-1-en-3-one

A mixture of lithium bromide (0.700 g, 8.06 mmol), lithium carbonate (1.20 g, 16.24 mmol) and anhydrous N,N-dimethylformamide (30 mL) were heated under nitrogen atmosphere to 95° C. To this mixture, (2α,5α,25R)-2-bromospirostan-3-one (4.00 g, 8.11 mmol) was added. The reaction mixture was stirred at 130° C. for 3 hours. After cooling to room temperature, the reaction mixture was diluted with ethyl acetate, washed with water (3x), brine (1x), dried (sodium sulfate), filtered and concentrated in vacuo to afford 3.31 g, (98%) of the title compound.
$^1$HNMR (250 MHz, CDCl$_3$) d 7.10 (d, J=10 Hz. 1H); 5.85 (d, J=10 Hz, 1H), 4.40 (q, J=7 Hz, 1H); 3.40 (m, 2H); 2.30 (m, 2H); 0.70–2.05 (m, 33H); 1.02 (s, 3H); 0.96 (d, J=7 Hz, 3H); 0.80 (s, 3H); 0.78 (d, J=7 Hz, 3H). MS 413 (M+H)$^+$.

PREPARATION H4

(1α,2α,5α,25R)-1,2-enoxy-spirostan-3-one

A mixture of (5α,25R)-spirost-1-en-3-one (2.87 g, 6.96 mmol), tetrahydrofuran (30 mL), methanol (50 mL) and 15% sodium hydroxide (1 mL) was stirred under nitrogen atmosphere. The mixture was cooled to 0° C. and 30% hydrogen peroxide (5 mL) was adried. The reaction mixture was gradually warmed to room temperature and stirred for 4 hours. The reaction was diluted with ethyl acetate, cooled to 0° C., and then quenched with saturated sodium bisulfite solution. The mixture was washed with saturated sodium bisulfite (2x), brine (1x), dried (sodium sulfate), filtered and concentrated in vacuo to give 2.64 g, (88%) of the title compound.
$^1$HNMR (250 MHz, CDCl$_3$) d 4.40 (q, J=7 Hz, 1H); 3.40 (m, 3H); 3.24 (d, J=6 Hz, 1H); 2.25 (dd, J=18, 4 Hz, 1H); 0.70–2.28 (m, 34H); 0.98 (d, J=7 Hz, 3H); 0.92 (s, 3H); 0.80 (s, 3H); 0.78 (d, J=7 Hz, 3H). MS 429 (M+H)$^+$.

PREPARATION H5

(1α,3β,5α,25R)-1,3-di(hydroxy)spirostane

Lithium aluminum hydride (0.43 g, 15.38 mmol) was added to a solution of (1α,2α,5α,25R)-1,2-epoxy-spirostan-3-one in THF (20 mL) at 0° C. The reaction was gradually warmed to room temperature and after 3 hours, additional lithium aluminum hydride (0.10 g, 3.58 mmol) was added. After 1 hour, the reaction was cooled to 0° C. and quenched by the sequential addition of $H_2O$ (0.75 mL), 15% NaOH (0.75 mL), and $H_2O$ (1.50 mL). The mixture was dried with $MgSO_4$, filtered, and concentrated in vacuo. The product was purified by flash chromatography (50% EtOAc/50% hexane to 95% EtOAc/5%MeOH) to afford 0.460 g, (34%) of the title compound.

$^1$HNMR (250 MHz, $CDCl_3$) d 4.48 (q, J=7 Hz, 1H); 4.04 (m, 1H); 3.80 (m, 1H); 3.40 (m, 2H); 0.75–2.05 (m, 37H); 0.96 (d, J=6 Hz, 3H); 0.84 (s, 3H); 0.78 (d, J=6 Hz, 3H); 0.76 (s, 3H). MS 433 (M+H)$^+$.

PREPARATION I1

(3β,5α,25R)-3-[(heptaacetyl-β-D-cellobiosyl)oxy]spirostan-1-one

Pyridinium chlorochromate (0.123, 0.67 mmol) was added to a mixture of (1α,3β,5α,25R)-3- [(heptaacetyl-β-D-cellobiosyl)oxy]-1-hydroxyspirostane (0.2 g, 0.19 mmol, see preparation B39), celite (0.2 g), in $CH_2Cl_2$ (5 mL) at 0° C. The reaction was allowed to come to ambient temperature and was stirred for 2 hours. The reaction was diluted with 15 mL $Et_2O$ and was filtered through a silica gel plug. The plug was washed with an additional 500 mL $Et_2O$. The filtrate was concentrated in vacuo to afford 0.18 g of the title compound (90%).

$^1$HNMR (250 MHz, $CDCl_3$) d 5.15 (m, 3H); 4.90 (m, 2H); 4.50 (m, 2H); 4.35 (m, 2H); 4.05 (m, 2H); 3.65 (m, 3H); 3.40 (m, 2H); 2.35 (t, J=12.5 Hz, 1H) 2.60 (q, J=6 Hz, 1H); 1.95–2.20 (m, 21H); 0.70–1.90 (m, 37H); 1.15 (s, 3H); 0.95 (d, J=7 Hz, 3H); 0.80 (d, J=6 Hz, 3H); 0.76 (s, 3H). MS: 1049 (M+H)$^+$.

PREPARATION J1

(3β,25R)-3-ethoxymethoxy,5-spirostene

A mixture of diosgenin (2.5 g, 6.0 mmol), chloromethyl ethyl ether (1.14 g, 12.0 mmol), diisopropylethylamine (3.90 g, 30.0 mmol) and 1,2-dichloroethane (75 mL) was stirred under nitrogen atmosphere at ambient temperature for 4 hours. Methanol (<1 mL) was added to quench the reaction. The mixture was diluted with ethyl acetate and washed with water (2x), brine (1x), dried over sodium sulfate, filtered and concentrated in vacuo to give 2.17 g (76.5%) of the title compound as a colorless solid.

$^1$H NMR (250 MHz, $CDCl_3$) d 5.35 (d, 2H, J=7.0 Hz); 4.75 (s, 2H); 4.4 (m, 1H);3,6 (q, 2H, J=7.0 Hz); 3.4 (m, 2H); 3.35 (t, 1H, J=11 Hz); 2.4–0.7 (m, 38H);1.2 (s, 3H); 0.95 (d, 3H, J=7 Hz); 0.8 (d, 3H, J=7 Hz); 0.75 (s, 3H). MS: 777 (M+Na)$^+$; mp 125°–127° C.

PREPARATION J2

(3β,5α,6α,25R)-3-ethoxy methoxy-6-hydroxyspirostane

Borane-tetrahydrofurancomplex (0.68 mL, 0.68 mmol) was added to a solution of (3β,25R)-3-ethoxymethoxy-5-spirostene (0.10 g, 0.21 mmol) in tetrahydrofuran (8 mL). The mixture was stirred under nitrogen atmosphere at ambient temperature for 3.5 hours. The reaction mixture was cooled to 0° C. and methanol (1.5 mL), 15% sodium hydroxide solution (1.5 mL) and 30% hydrogen peroxide (1.5 mL) were added. The reaction mixture was then gradually warmed to ambient temperature and stirred overnight.

The reaction was quenched at 0° C. by the addition of saturated sodium bisulfite solution. The mixture was diluted with ethyl acetate and washed with ammonium chloride solution (1x), brine (1x), dried (sodium sulfate), filtered and concentrated in vacuo to give 0.11 g of a mixture of the 6α-alcohol and the 6β-alcohol. The two products were separated by flash chromatography on silica gel (6:4 hexane/ethyl acetate). The major product (Rf=0.40) was identified to be the title compound.

$^1$H NMR (250 MHz; $CDCl_3$) d 4.7 (s, 2H); 4.4 (m, 1H); 3.6 (q, 2H, J=11.0 Hz);3.45 (m, 3H); 3.35 (t, 1H, J=11.0 Hz); 2.3–0.6 (m, 41H); 1.8 (d, 3H, J=7.0 Hz);0.82 (s, 3H), 0.78 (d, 3H, J=7.0 Hz); 0.76 (s, 3H). MS: 491 (M+H)$^+$; mp 171° C.

PREPARATION J3

(3β,5α,25R)-3-ethoxymethoxy-spirostan-6-one

Pyridinium chlorochromate (1.98 g, 9.20 mmol) was added to a mixture of (3β,5α,6α,25R)-3-ethoxy methoxy-6-hydroxyspirostane (0.90 g, 1.8 mmol) and celite (8.0 g) in anhydrous dichloromethane at 0° C. The reaction mixture was gradually warmed to ambient temperature over 1 hour and allowed to stir for an additional 5 hours. The reaction mixture was then filtered through a plug of silica gel using ether as the eluent. The combined ether fractions were concentrated in vacuo to afford 0.80 g (91%) of the title compound as a colorless solid. $^1$H NMR (250 MHz; $CDCl_3$) d 4.75 (m, 2H); 4.4 (m, 1H); 3.6 (q, 2H, J=7.0 Hz); 3.45 (m, 2H); 3.35 (t, 1H, J=11.0 Hz); 2.4–0.6 (m, 40H); 0.9 (d, 3H, J=7.0 Hz); 0.8 (d, 3H, J=7.0 Hz); 0.78 (s, 6H). MS: 489.0 (M+H)$^+$; mp 191–1930C.

PREPARATION J4

(3β,5α,25R)-spirostan-6-one

Concentrated hydrochloric acid (2 drops) was added to a solution of (3β,5α,25R)-3-ethoxymethoxy-spirostan-6-one (0.70 g, 1.43 mmol) in methanol (10 mL) and tetrahydrofuran (10 mL). The mixture was stirred under nitrogen atmosphere and heated to 62° C. After 15 minutes, the reaction was cooled to 0° C. and neutralized with 15% sodium hydroxide solution. The mixture was concentrated in vacuo then diluted with ethyl acetate. The organic layer was washed with water (2x), brine (1 x), dried (sodium sulfate), concentrated in vacuo and purified by flash chromatography (1:1 hexane/ethyl acetate) to afford 0.55 g (89.4%) of the title compound as a colorless solid.

$^1$H NMR (250 MHz; $CDCl_3$) d 4.4 (m, 1H); 3.45 (m, 2H); 3.35 (t, 1H,J=11.0 Hz);2.35–0.6 (m, 38H); 0.95 (d, 3H, J=7.0 Hz); 0.75 (d, 3H, J=7.0); 0.71 (s,6H). MS: 431 (M+H)$^+$; mp 210°–212° C.

PREPARATION K1

(3β,5α,6α,25R)-3-[(heptaacetyl-β-D-cellobiosyl)oxy]6-hydroxyspirostane

Sodium borohydride (0.11 g, 2.86 mmol) was added to a solution of (3β,5α,25R)-3-[(heptaacetyl-β-D-cellobiosyl)oxy]spirostan-6-one (1.5 g, 1.43 see preparation B41) in ethanol (20 mL) and dichloromethane (5 mL) and the mixture was stirred under nitrogen atmosphere at room temperature for 4 hours. The reaction mixture was then cooled to 0° C. and was neutralized with 1N hydrochloric acid. The mixture was partially concentrated in vacuo and then was diluted with ethyl acetate, washed with 1N hydrochloric acid (1x), brine (1x), dried (sodium sulfate), filtered and concentrated in vacuo to afford 1.00 g (66%) of the title compound as a colorless solid.

$^1$H NMR (250 MHz; CDCl$_3$) d 5.2–4.4 (m, 14H); 4.3 (m, 1H); 3.75–3.35 (m, 3H); 3.3 (t, 1H, J=11.0 Hz); 2.15–0.5 (m, 59H); 0.95 (s, 3H); 0.90 (d, 3H, J=7.0 Hz); 0.75 (s, 3H); 0.70 (d, 3H, J=7.0 Hz). MS: 1051 (M+H)$^+$.

It should be understood that the invention is not limited to the particular embodiments shown and described herein, but that various changes and modifications may be made without departing from the spirit and scope of this novel concept as defined by the following claims.

We claim:

1. A spirostanyl glycoside of Formula IA

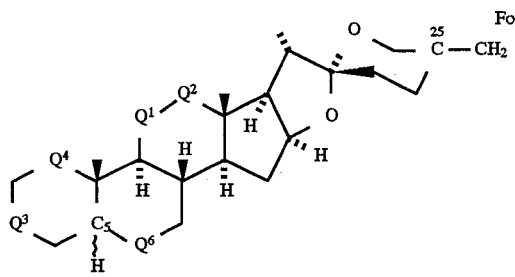

Formula IA wherein either (A):

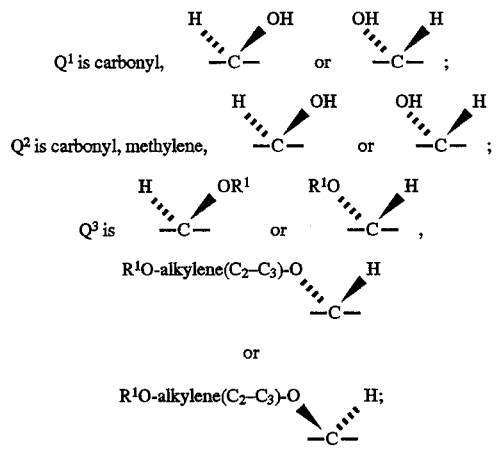

Q$^4$ and Q$^5$ are both methylene;
C$_{25}$ is (R);
and wherein
R$^1$ is
β-D-glucopyranosyl,
β-D-glucopyranuronosyl,
β-D-2-acetamido-2-deoxy-glucopyranosyl,
β-D-galactopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
α-D-cellobiosyl,
β-D-cellobiosyl,
β-D-lactosyl,
β-D-maltosyl,
β-D-gentiobiosyl,
3-O-β-D-galactopyrasnosyl-α-D-arabanopyranosyl or
β-D-maltotriosyl.

2. A compound according to claim 1 wherein Q$^1$ is carbonyl,

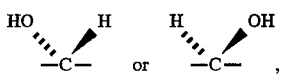

Q$^2$, Q$^4$ and Q$^5$ are each methylene, Q$^3$ is

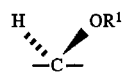

and the C$_5$ hydrogen is alpha.

3. A compound according to claim 2 wherein Q$^1$ is carbonyl and R$^1$ is β-D-cellobiosyl.

4. A compound according to claim 2 wherein Q$^1$ is carbonyl and R$^1$ is β-D-galactopyranosyl.

5. A compound according to claim 2 wherein Q$^1$ is carbonyl and R$^1$ is α-D-cellobiosyl.

6. A compound according to claim 2 wherein Q$^1$ is carbonyl and R$^1$ is β-D-glucopyranosyl.

7. A compound according to claim 2 wherein Q$^1$ is carbonyl and R$^1$ is β-D-lactosyl.

8. A compound according to claim 2 wherein Q$^1$ is carbonyl and R1 is β-D-maltosyl.

9. A compound according to claim 2 wherein Q$^1$ is carbonyl and R1 is β-D-maltotriosyl.

10. A compound according to claim 2 wherein Q$^1$ is

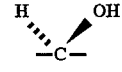

and R$^1$ is β-D-cellobiosyl.

11. A compound according to claim 2 wherein Q$^1$ is

and R$^1$ is β-D-cellobiosyl.

12. A compound according to claim 1 wherein Q$^1$ is carbonyl,

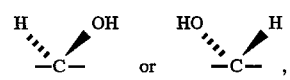

Q$^2$ is carbonyl,

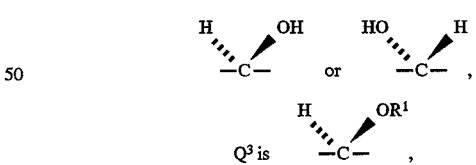

Q$^4$ and Q$^5$ are each methylene and the C$_5$ hydrogen is alpha.

13. A compound according to claim 12 wherein Q$^1$ is carbonyl, Q$^2$ is carbonyl and R$^1$ is β-D-cellobiosyl.

14. A compound according to claim 12 wherein Q$^1$ is carbonyl, Q$^2$ is

and R$^1$ is β-D-cellobiosyl.

15. A compound according to claim 12 wherein Q$^1$ is carbonyl, Q$^2$ is

and R¹ is β-D-lactosyl.

16. A compound according to claim 12 wherein Q¹ is

Q² is carbonyl and R¹ is β-D-cellobiosyl.

17. A compound according to claim 12 wherein Q¹ is

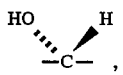

Q² is carbonyl and R¹ is β-D-cellobiosyl.

18. The pharmaceutical composition for the treatment of hypercholesterolemia or atherosclerosis in mammals which comprises a compound of claim 1 and a pharmaceutically acceptable carrier.

19. The composition comprising a hydrate of a compound according to claim 1.

20. A method for treating hypercholesterolemia or atherosclerosis in a mammal comprising adminstering to a mammal suffering from hypocholesterolemia or atherosclerosis a hypercholesterolemia or atherosclerosis treating amount of a Formula I spirostanyl glycoside

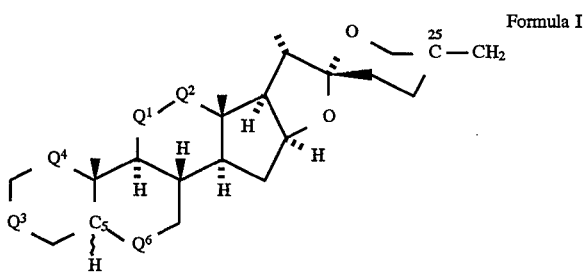

wherein either (A):

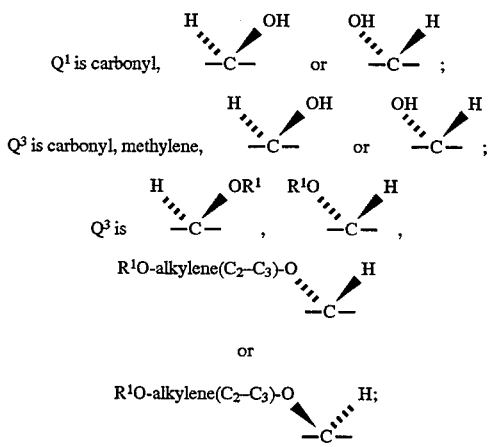

Q⁴ and Q⁵ are both methylene;
C₂₅ is (R);
and wherein
R¹ is
β-D-glucopyranosyl,
β-D-glucopyranuronosyl,
β-D-2-acetamido-2-deoxy-glucopyranosyl,
β-D-galactopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
α-D-cellobiosyl,
β-D-cellobiosyl,
β-D-lactosyl,
β-D-maltosyl,
β-D-gentiobiosyl,
3-O-β-D-galactopyranosyl-α-D-arabanopyranosyl or
β-D-maltotriosyl.

21. The method according to claim 20 wherein Q¹ is carbonyl,

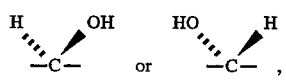

Q², Q⁴ and Q⁵ are each methylene, Q³ is

and the C₅ hydrogen is alpha.

22. The method according to claim 21 wherein Q¹ is carbonyl and R¹ is β-D-cellobiosyl.

23. The method according to claim 21 wherein Q¹ is carbonyl and R¹ is β-D-galactopyranosyl.

24. The method according to claim 21 wherein Q¹ is carbonyl and R¹ is α-D-cellobiosyl.

25. The method according to claim 21 wherein Q¹ is carbonyl and R¹ is β-D-glucopyranosyl.

26. The method according to claim 21 wherein Q¹ is carbonyl and R¹ is β-D-maltosyl.

27. The method according to claim 21 wherein Q¹ is carbonyl and R¹ is β-D-maltotriosyl.

28. The method according to claim 21 wherein Q¹ is carbonyl and R¹ is β-D-lactosyl.

29. The method according to claim 21 wherein Q¹ is

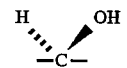

and R¹ is β-D-cellobiosyl.

30. The method according to claim 21 wherein Q¹ is

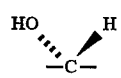

and R¹ is β-D-cellobiosyl.

31. The method according to claim 20 wherein Q¹ is carbonyl,

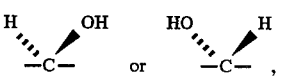

$Q^2$ is carbonyl,

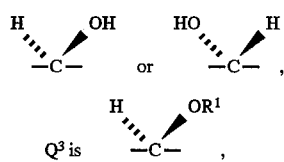 , $Q^3$ is  , $Q^4$ and $Q^5$ are each methylene and the $C_5$ hydrogen is alpha.

32. The method according to claim 31 wherein $Q^1$ is carbonyl, $Q^2$ is carbonyl and $R^1$ is β-D-cellobiosyl.

33. The method according to claim 31 wherein $Q^1$ is carbonyl, $Q^2$ is

and $R^1$ is β-D-cellobiosyl.

34. The method according to claim 31 wherein $Q^1$ is carbonyl, $Q^2$ is

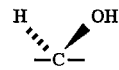

and $R^1$ is β-D-lactosyl.

35. The method according to claim 31 wherein $Q^1$ is

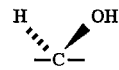 , $Q^2$ is carbonyl and $R^1$ is β-D-cellobiosyl.

36. The method according to claim 31 wherein $Q^1$ is a

 , $Q^2$ is carbonyl and $R^1$ is β-D-cellobiosyl.

* * * * *